United States Patent
Ujiie et al.

(10) Patent No.: US 10,566,548 B2
(45) Date of Patent: Feb. 18, 2020

(54) IMAGE SENSOR, STACKED IMAGING DEVICE AND IMAGING MODULE

(71) Applicant: SONY CORPORATION, Tokyo (JP)

(72) Inventors: Yasuharu Ujiie, Kanagawa (JP); Masaki Murata, Tokyo (JP); Yuya Kumagai, Tokyo (JP); Hideaki Mogi, Kanagawa (JP); Shintarou Hirata, Tokyo (JP)

(73) Assignee: Sony Corporation, Tokyo (JP)

( * ) Notice: Subject to any disclaimer, the term of this patent is extended or adjusted under 35 U.S.C. 154(b) by 67 days.

(21) Appl. No.: 15/572,609

(22) PCT Filed: Apr. 19, 2016

(86) PCT No.: PCT/JP2016/062377
§ 371 (c)(1),
(2) Date: Nov. 8, 2017

(87) PCT Pub. No.: WO2016/185858
PCT Pub. Date: Nov. 24, 2016

(65) Prior Publication Data
US 2018/0114926 A1 Apr. 26, 2018

(30) Foreign Application Priority Data
Jan. 19, 2016 (JP) ................ 2016-007706

(51) Int. Cl.
*H01B 1/12* (2006.01)
*H01L 51/00* (2006.01)
(Continued)

(52) U.S. Cl.
CPC ........ *H01L 51/0074* (2013.01); *H01B 1/12* (2013.01); *H01L 27/307* (2013.01);
(Continued)

(58) Field of Classification Search
CPC ........... C07D 495/04; H01L 2251/301; H01L 27/146; H01L 27/307; H01L 51/00;
(Continued)

(56) References Cited

U.S. PATENT DOCUMENTS

2017/0040550 A1* 2/2017 Yakushiji ............. H01L 27/146

FOREIGN PATENT DOCUMENTS

| JP | 2009-275032 A | 11/2009 |
| JP | 2010-232413 A | 10/2010 |
| JP | 2011-176259 A | 9/2011 |
| JP | 2013-138173 A | 7/2013 |

(Continued)

OTHER PUBLICATIONS

International Search Report prepared by the Japan Patent Office dated Jun. 30, 2016, for International Application No. PCT/JP2016/062377.

(Continued)

*Primary Examiner* — Mark Kopec
*Assistant Examiner* — Jaison P Thomas
(74) *Attorney, Agent, or Firm* — Sheridan Ross P.C.

(57) ABSTRACT

An image sensor includes at least a first electrode, a second electrode, an organic photoelectric conversion layer, and a carrier blocking layer. The carrier blocking layer is formed of a material having the following structural formula (1), and has a thickness of from $5 \times 10^{-9}$ to $1.5 \times 10^{-7}$ m:

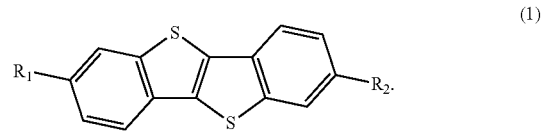

10 Claims, 7 Drawing Sheets

(51) Int. Cl.
  *H01L 51/42* (2006.01)
  *H01L 27/30* (2006.01)
  *H01L 51/44* (2006.01)

(52) U.S. Cl.
  CPC ...... *H01L 51/0058* (2013.01); *H01L 51/0072* (2013.01); *H01L 51/0078* (2013.01); *H01L 51/42* (2013.01); *H01L 51/442* (2013.01); *H01L 2251/301* (2013.01)

(58) Field of Classification Search
  CPC ............. H01L 51/0058; H01L 51/0072; H01L 51/0074; H01L 51/0078; H01L 51/42; H01L 51/4273; H01L 51/442; Y02E 10/549; H01B 1/12
  See application file for complete search history.

(56) References Cited

FOREIGN PATENT DOCUMENTS

| | | |
|---|---|---|
| JP | 2015-163595 A | 9/2015 |
| WO | WO 2006/077888 A1 | 7/2006 |
| WO | WO 2009/122956 A1 | 10/2009 |
| WO | WO 2012/121393 A1 | 9/2012 |
| WO | WO 2014/178923 | 11/2014 |
| WO | WO 2015/163349 A1 | 10/2015 |

OTHER PUBLICATIONS

Extended European Search Report for European Patent Application No. 16796252.1, dated Dec. 11, 2018, 6 pages.

\* cited by examiner

IMAGE SENSOR, STACKED IMAGING DEVICE AND IMAGING MODULE

CROSS REFERENCE TO RELATED APPLICATIONS

This application is a national stage application under 35 U.S.C. 371 and claims the benefit of PCT Application No. PCT/JP2016/062377 having an international filing date of 19 Apr. 2016, which designated the United States, which PCT application claimed the benefit of Japanese Patent Application No. 2015-101718 filed 19 May 2015, and Japanese Patent Application No. 2016-007706 filed 19 Jan. 2016, the disclosures of which are incorporated herein by reference in their entirety.

TECHNICAL FIELD

The present disclosure relates to an image sensor, a stacked imaging device, and an imaging module.

BACKGROUND ART

In recent years, to meet various applications, image sensors have been improved in performance and diversified in function, and are still in continuous evolution. As one of next generation technologies, photoelectric conversion by organic semiconductor materials instead of by inorganic semiconductor materials can be mentioned. These image sensors are called "organic image sensors." Further, image sensors (called "stacked imaging devices") which have spectral sensitivity corresponding to red color, green color and blue color owing to the stacking of plural organic semiconductor layers, are under development, and are attracting interest. These stacked imaging devices do not require a color separation optical system and can extract, from a single pixel, three kinds of electrical signals (image signals) corresponding to red color, green color and blue color, and therefore are high in light availability and large in opening and hardly generate false signals such as moiré. With an image sensor having a conventional color filter, approximately 40% of transmitted light is said to be lost due to absorption by transmission through the color filter.

At present, image sensors that use silicon (Si) as a photoelectric conversion material dominate.

Miniaturization of pixels for improvements in recording density has been advancing, and the pixel size has reached approximately 1 sm. The light absorption coefficient of Si is from $10^3$ to $10^4$ cm$^{-1}$ or so in the visible light region, and a photoelectric conversion layer in an image sensor is generally located at a depth of 3 µm or greater in a silicon semiconductor substrate. As the miniaturization of the pixel size proceeds, the aspect ratio of the pixel size to the depth of a photoelectric conversion layer increases, consequently leading to leakage of light from adjacent pixels, a restriction to the incident angle of light, and a reduction in the performance of the image sensor. As a solution to such problems, organic materials having a large absorption coefficient are attracting interest. Organic materials have an absorption coefficient of $10^5$ cm$^{-1}$ or so or greater in the visible light region. In an organic image sensor or stacked imaging device, such an organic material makes it possible to form a photoelectric conversion layer with a reduced thickness, and therefore is considered to realize an improvement in sensitivity and an increase in the number of pixels while preventing false colors. Accordingly, developments of these organic materials are diligently under way.

Organic image sensors are considered to have many advantages as described above, but a capacity reduction of the resulting imaging module can be mentioned as one of problems. The term "imaging module" as used herein means a unit that includes a plurality of built-in organic image sensors and outputs electrical signals, which have been obtained through photoelectric conversion, as an image. Charge obtained under irradiation of light in the photoelectric conversion layer that forms each organic image sensor is converted into a voltage, which is then outputted as an electrical signal (image signal). At this time, if the total electric capacity C is large including, in addition to the electric capacity of the organic image sensor, those of peripheral components such as a floating diffusion (hereinafter abbreviated as "FD"), a buffer amplifier connected to the FD, and a reset gate and horizontal output gate adjacent the FD, the voltage change per charge becomes smaller, resulting in a smaller signal-to-noise (S/N) ratio and deteriorated image quality. Now, the voltage V of an electrical signal is represented by:

$$V=Q/C$$

(Q: quantity of electric charge). Consequently, as the electric capacity of the organic image sensor increases, V decreases, and as a result, electrical signals become weaker. It is to be noted that the electric capacity of the organic image sensor (specifically, the electric capacity of the organic layer to be described next) accounts for approximately a half of the total electric capacity C. Further, the electric capacity $C_0$ is generally represented by:

$$C_0=(\varepsilon \cdot S_0)/d_0$$

($\varepsilon$: dielectric constant, $S_0$: area, $d_0$: thickness)

Therefore, as factors that affect the capacity reduction of the organic image sensor, the pixel area, the dielectric constants of materials forming the organic image sensor and the thickness of the organic layer in the organic image sensor can be mentioned. If a capacity reduction is attempted depending on the thickness, there is a need to increase the total thickness of the organic layer in the organic image sensor.

As illustrated by way of example in a concept diagram of FIG. 1A, the organic layer has a stacked structure of a carrier blocking layer (first carrier blocking layer) 22, an organic photoelectric conversion layer 23 and a second carrier blocking layer 24, which are all held between a first electrode 21 and a second electrode 25. It is possible to increase the thickness of the organic photoelectric conversion layer 23. However, the organic photoelectric conversion layer 23 is a layer that takes part in the photoelectric conversion function, so that it is often difficult to achieve both thickening and the avoidance of a reduction in photoelectric conversion efficiency upon photoelectric conversion of light of a specific wavelength. Further, if the material forming the organic photoelectric conversion layer 23 in a stacked imaging device has spectral characteristics that also absorb light of wavelengths other than the desired wavelength, the thickening of the organic photoelectric conversion layer 23 has a potential problem of shielding light that the photoelectric conversion layer, which forms the image sensor located in a lower part, is supposed to absorb. The second carrier blocking layer 24 also needs to have a function to transport electrons. If the thickness of the second carrier blocking layer 24 formed of an organic material with low electron mobility is increased, the second carrier blocking layer 24 acts as a resistant component, thereby making it difficult to maintain a high photoelectric conversion efficiency.

Incidentally, the mother skeletons of the following structural formulas (1), (2) and (3) are materials well-known as organic thin-film transistor (organic TFT) materials, and are called "benzothienobenzothiophene (BTBT) materials." JP 2010-232413A discloses the use BTBT materials in organic TFTs, static induction transistors and solar cells, but makes no mention about their use in image sensors. This patent publication also discloses the use BTBT materials as active layers, and their use in a wide thickness range of 1 nm to 10 µm, preferably from 5 nm to 5 µm, more preferably from 10 nm to 3 µm. In the Examples, the thickness of the BTBT material is set at 250 nm. Moreover, no spectral characteristics are required for the active layers themselves, and no reference is made to electric capacity. WO 2012/121393A1 discloses a technology that liquid crystal is developed using BTBT materials and are used in organic TFTs. However, in this international publication, nothing is mentioned about image sensors, no reference is made to spectral characteristics, and no mention is made about electric capacity.

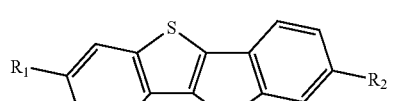

(1)

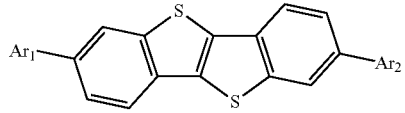

(2)

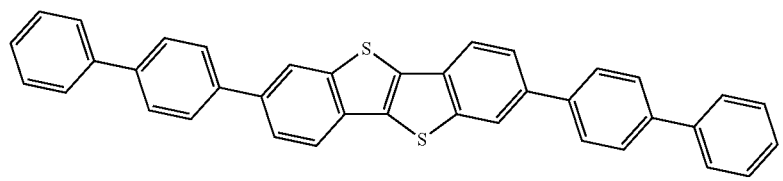

(3)

CITATION LIST

Patent Literature

[PTL 1]
JP 2010-232413A
[PTL 2]
WO 2012/121393A1
[PTL 3]
JP 2011-176259A

SUMMARY

Technical Problems

The first carrier blocking layer in the organic image sensor is often called "an electron blocking layer," and is generally formed from a carbazole material or aromatic amine material, for example, as disclosed in JP 2011-176259A. It has, however, been found that, if a capacity reduction is attempted by increasing the thickness of the first carrier blocking layer, the formation of the first carrier blocking layer from the carbazole material or aromatic amine material leads to a significant reduction in external quantum efficiency and a marked increase in dark current as will be described subsequently herein, for example, when the thickness of the first carrier blocking layer is increased, and that the carbazole material or aromatic amine material is not suited for practical applications.

Therefore, the present disclosure has as first, second and third objects thereof the provision of an image sensor of a configuration that problems such as a reduction in external quantum efficiency and an increase in dark current hardly arise, and a stacked imaging device and an imaging module formed of such image sensors.

Solution to Problems

An image sensor according to a first aspect of the present disclosure for achieving the above-described first object includes at least a first electrode, a second electrode, an organic photoelectric conversion layer, and a carrier blocking layer.

The carrier blocking layer is formed of a material having the following structural formula (1), and has a thickness of from $5 \times 10^{-9}$ to $1.5 \times 10^{-7}$ m, preferably from $5 \times 10^{-9}$ to $1.0 \times 10^{-7}$ m:

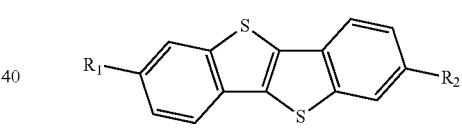

(1)

wherein $R_1$ and $R_2$ are independently a group selected from H, an aryl group and an alkyl group, the aryl group is a group selected from the group consisting of phenyl, biphenyl, terphenyl, naphthyl, naphthylphenyl, tolyl, xylyl, C2-C6 alkyl-substituted phenyl, anthracenyl, anthracenylphenyl, phenanthryl, phenanthrylphenyl, pyrenyl, pyrenylphenyl, tetracenyl, tetracenylphenyl, fluoranthenyl, fluoranthenylphenyl, pyridinyl, pyridinylphenyl, quinolinyl, quinolylphenyl, acridinyl, acridinylphenyl, indol, indolylphenyl, imidazol, imidazolylphenyl, benzimidazole, benzimidazolylphenyl, thienyl, and thienyelphenyl, and the alkyl group is a group selected from the group consisting of methyl, ethyl, propyl, butyl, pentyl, and hexyl, which is a straight-chain alkyl group or a branched alkyl group.

An image sensor according to a second aspect of the present disclosure for achieving the above-described first object includes at least a first electrode, a second electrode, an organic photoelectric conversion layer, and a carrier blocking layer.

The carrier blocking layer is formed of a material having the following structural formula (2), and has a thickness of from $5 \times 10^{-9}$ to $1.5 \times 10^{-7}$ m, preferably from $5 \times 10^{-9}$ to $1.0 \times 10^{-7}$ m:

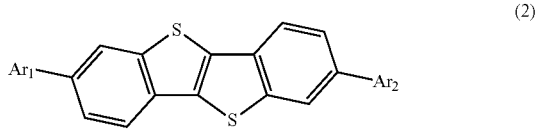

(2)

wherein $Ar_1$ and $Ar_2$ are independently a substituted or unsubstituted aryl group, which is selected from the group consisting of phenyl, biphenyl, terphenyl, naphthyl, naphthylphenyl, tolyl, xylyl, C2-C6 alkyl-substituted phenyl, anthracenyl, anthracenylphenyl, phenanthryl, phenanthrylphenyl, pyrenyl, pyrenylphenyl, tetracenyl, tetracenylphenyl, fluoranthenyl, fluoranthenylphenyl, pyridinyl, pyridinylphenyl, quinolinyl, quinolylphenyl, acridinyl, acridinylphenyl, indol, indolylphenyl, imidazol, imidazolylphenyl, benzimidazole, benzimidazolylphenyl, thienyl, and thienylphenyl.

An image sensor according to a third aspect of the present disclosure for achieving the above-described first object includes at least a first electrode, a second electrode, an organic photoelectric conversion layer, and a carrier blocking layer.

The carrier blocking layer is formed of a material having the following structural formula (3), and has a thickness of from $5 \times 10^{-9}$ to $1.5 \times 10^{-7}$ m, preferably from $5 \times 10^{-9}$ to $1.0 \times 10^{-7}$ m:

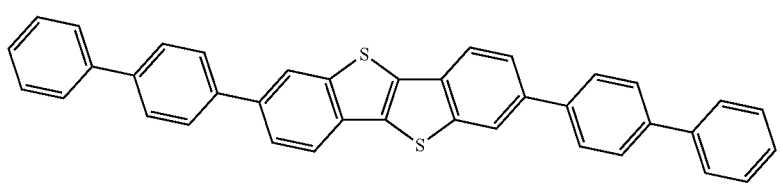

(3)

A stacked imaging device (vertically spectral imaging device) according to the present disclosure for achieving the above-described second object includes at least two image sensors according to one of the first to third aspects of the present disclosure, which are stacked together.

An imaging module according to a first aspect of the present disclosure for achieving the above-described third object includes a plurality of image sensors according to one of the first to third aspects of the present disclosure. The imaging module according to the first aspect of the present disclosure as described above may have a configuration that a blue image sensor, a green image sensor and a red image sensor are disposed in a plane as in a Bayer array. An imaging module according to a second aspect of the present disclosure for achieving the above-described third object includes a plurality of stacked imaging devices of the present disclosure.

Advantageous Effects of Invention

In the image sensors according to the first to third aspects of the present disclosure, the image sensors forming the stacked imaging device of the present disclosure, and the image sensors forming the imaging modules of the first and second aspects of the present disclosure (these image sensors will hereinafter be collectively called "the image sensor or the like of the present disclosure"), each carrier blocking layer is formed from the material which has the structural formula (1), (2) or (3) and does not absorb much visible light. The carrier blocking layer, therefore, does not interfere with the photoelectric conversion by the image sensor, in which the carrier blocking layer is included, or the image sensor, which is located as a lower layer as viewed in the direction of incident light, and can achieve both good external quantum efficiency and spectral characteristics. Further, the carrier blocking layer can suppress a dark current, and can also improve the dark current vs. voltage characteristics. Furthermore, the electric capacity can be reduced. In addition, it is possible to achieve an improvement in so-called residual image characteristics. As a consequence of the foregoing advantageous effects, beautiful imaging is feasible, and moreover an imaging module that hardly produces residual images can be realized. It is to be noted that the advantageous effects described herein are merely illustrative and not limiting, and that other additional advantageous effect or effects may also be available.

DESCRIPTION OF EMBODIMENTS

Figure 1A:
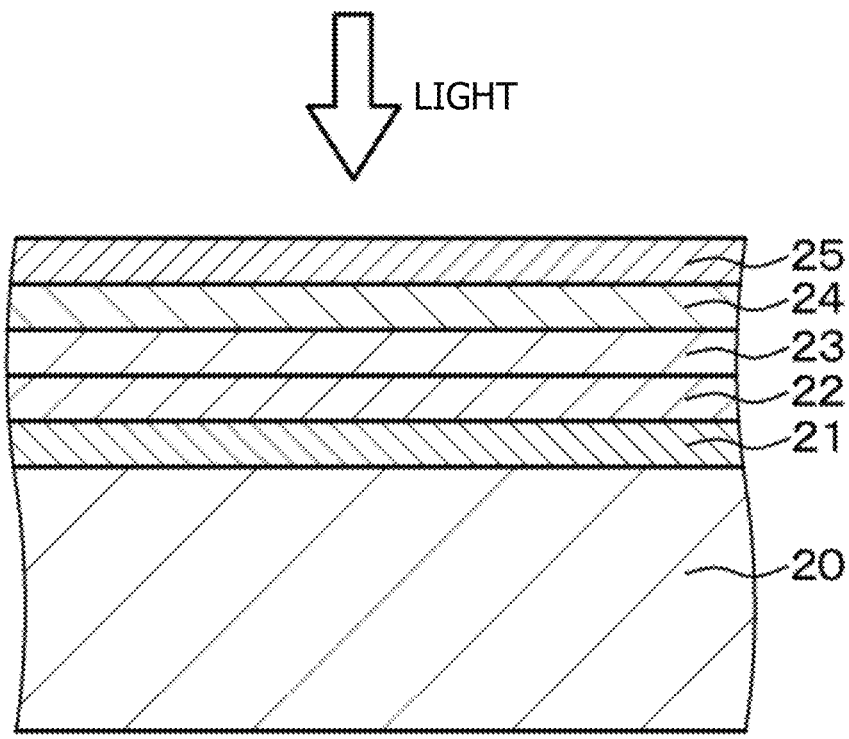
FIGS. 1A and 1B are concept diagrams of image sensors of Example 1.

With reference to the drawings, the present disclosure will hereinafter be described based on Examples. However, the present disclosure is not limited to the Examples, and various numerical values and materials in the Examples are merely illustrative. The description will be made in the following order.

1. General Description of Image Sensors According to First Aspect to Third Aspect of Present Disclosure, Stacked Imaging Device of Present Disclosure, and Imaging Modules According to First Aspect and Second Aspect of Present Disclosure
2. Example 1 (Image Sensors According to First Aspect to Third Aspect of Present Disclosure, and Imaging Module According to First Aspect of Present Disclosure)
3. Example 2 (Modification of Example 1)
4. Example 3 (Modifications of Example 1 and Example 2, Stacked Image Sensor of Present Disclosure, and Imaging Module According to Second Aspect of Present Disclosure)
5. Others General Description of Image Sensors According to First Aspect to Third Aspect of Present Disclosure, Stacked Imaging Device of Present Disclosure, and Imaging Modules According to First Aspect and Second Aspect of Present Disclosure A configuration that three kinds of image sensors are stacked in a vertical direction can be mentioned. Specifically, these three kinds of image sensors consist of an image sensor (called the "blue image sensor" for the sake of convenience) according to one of the first to third aspects of the present disclosure, which is provided with an organic photoelectric conversion layer that absorbs blue light (light of from 425 to 495 nm) and has sensitivity to blue color; another image sensor (called the "green image sensor" for the sake of convenience) according to one of the first to third aspects of the present disclosure, which is provided with an organic photoelectric conversion layer that absorbs green light (light of from 495 to 570 nm) and has sensitivity to green color; and a further image sensor (called the "red image sensor" for the sake of convenience) according to one of the first to third aspects of the present disclosure, which is provided with an organic photoelectric conversion layer that absorbs red light (light of from 620 to 750 nm) and has sensitivity to red color. As the order of stacking of these image sensors, it may be preferred to stack the blue image sensor, the green image sensor and the red image sensor in this order in the direction of incident light, or the green image sensor, the blue image sensor and the red image sensor in this order in the direction of incident light, because light of shorter wavelengths is more efficiently absorbed on the side of an entrance surface. As red color has longest wavelengths among the three colors, it is preferred to place the red image sensor as the lowest layer as viewed from the entrance surface of light. As an alternative, it is possible to adopt a configuration that an image sensor having sensitivity to red color is formed in a silicon semiconductor substrate and a green image sensor and a blue image sensor are formed on the silicon semiconductor substrate; or a configuration that two kinds of image sensors are formed in a silicon semiconductor substrate and the remaining one kind of image sensor according to one of the first to third aspects of the present disclosure is formed on the silicon semiconductor substrate. The image sensor formed on the silicon semiconductor substrate may preferably be of the back-illuminated type, but may also be provided as the front-illuminated type. Examples of an inorganic material that forms the photoelectric conversion layer may include, in addition to crystalline silicon, amorphous silicon, microcrystalline silicon, crystalline selenium, and amorphous selenium; and compound semiconductors such as chalcopyrite compounds [CIGS (CuInGaSe), CIS (CuInSe$_2$), CuInS$_2$, CuAlS$_2$, CuAlSe$_2$, CuGaS$_2$, CuGaSe$_2$, AgAlS$_2$, AgAlSe$_2$, AgInS$_2$, AgInSe$_2$], or group III-V compounds (GaAs, InP, AlGaAs, InGaP, AlGaInP, InGaAsP), CdSe, CdS, In$_2$Se$_3$, In$_2$S$_3$, Bi$_2$Se$_3$, Bi$_2$S$_3$, ZnSe, ZnS, PbSe, and PbS. In addition, quantum dots made from one or more of these materials can also be used in the inorganic photoelectric conversion layer. Moreover, a single-plate color solid-state imaging module can be configured with the imaging module according to one of the first and second aspects of the present disclosure.

In the imaging module according to the second aspect of the present disclosure which is provided with a plurality of stacked imaging devices, image sensors with sensitivity to light of plural wavelengths are stacked in the incident direction of light in the same pixels, different from an imaging module provided with image sensors in a Bayer array (in other words, instead of performing the spectroscopy of blue color, green color and red color through color filters). It is, therefore, possible to achieve an improvement in sensitivity and also an improvement in pixel density per unit volume. Further, the organic material has a high absorption coefficient. Therefore, the thickness of the organic photoelectric conversion layer can be made small compared with those of conventional Si-based photoelectric conversion layers, whereby the leakage of light from adjacent pixels and the restriction to the incident angle of light are reduced. Furthermore, with a conventional Si-based image sensor, false colors are produced because color signals are generated by performing interpolation processing among the pixels of three colors. With the imaging module according to the second aspect of the present disclosure which is provided with stacked imaging devices, the production of false colors is suppressed. In the imaging module according to the first aspect of the present disclosure, on the other hand, the use of color filters can mitigate the requirements for spectral characteristics for blue color, green color and red color, and can provide high mass productivity.

The image sensor or the like of the present disclosure can be formed in, but is not limited to, a structure that the first electrode serves as a cathode, the second electrode serves as an anode, and the carrier blocking layer is arranged between the first electrode and the organic photoelectric conversion layer.

In the image sensor or the like of the present disclosure including the preferred structure described above, the carrier blocking layer may preferably have as small a light absorbance as possible in the visible light region so that the photoelectric conversion function of the organic photoelectric conversion layer is not interfered with. The image sensor or the like of the present disclosure may be configured so that the light absorbance of the carrier blocking layer is 3% or less at 450 nm wavelength, 30% or less at 425 nm wavelength, and 80% or less at 400 nm wavelength when the thickness of the carrier blocking layer is converted to 150 nm. Therefore, the carrier blocking layer formed from the material having the above-described structural formula (1), (2) or (3) is also excellent in spectral characteristics. In general, many of organic compounds have a high light absorption intensity in a wavelength region on the side of wavelengths shorter than 450 nm, and therefore involve a problem that they absorb blue light which should be absorbed in the organic photoelectric conversion layer of the image sensor. In the image sensor or the like of the present disclosure, on the other hand, the material that forms the carrier blocking layer has excellent light absorption characteristics and does not interfere with the photoelectric conversion function of the image sensor.

In the image sensor or the like of the present disclosure including the various preferred structures described above, the carrier blocking layer is desirably formed of a material having a carrier mobility of $9 \times 10^{-4}$ cm$^2$/V·s or higher, preferably $9 \times 10^{-3}$ cm$^2$/V·s or higher, more preferably $6 \times 10^{-2}$ cm$^2$/V·s or higher.

In the image sensor or the like of the present disclosure including the various preferred structures described above, when light of 560 nm wavelength is irradiated at 2 µW/cm$^2$ while applying −3 V between the second electrode and the first electrode and the irradiation of light is then stopped, $T_0$ may desirably be 10 milliseconds or less where $T_0$ is a time from the stop of the irradiation of light until a quantity of current decreases to $0.03 \times I_0$ ($I_0$: quantity of current flowing between the second electrode and the first electrode immediately before the stop of the irradiation of light).

In the image sensor or the like of the present disclosure including the various preferred structures described above, upon irradiation of light and photoelectric conversion in the organic photoelectric conversion layer, holes and electrons are carrier-separated. The electrode from which holes are extracted is defined as "the cathode," while the electrode from which electrons are extracted is defined as "the anode." Upon formation of the stacked imaging device, the first electrode and the second electrode can be formed from a transparent conductive material. If image sensors or the like of the present disclosure are disposed in a plane, for example, as in a Bayer array, one of the first electrode and the second electrode can be formed of a transparent conductive material, and the other electrode can be formed of a metal material. In this case, the first electrode located on the side of incident light can be formed of a transparent conductive material, and the second electrode can be formed of Al (aluminum), Al—Si—Cu (an alloy of aluminum, silicon and copper) or Mg—Ag (an alloy of magnesium and silver); or as an alternative, the second electrode located on the side of incident light can be formed of a transparent conductive material, and the first electrode can be formed of Al—Nd (an alloy of aluminum and neodymium) or ASC (an alloy of aluminum, samarium and copper). An electrode formed of a transparent conductive material may be called "a transparent electrode." As the transparent conductive material that forms the transparent electrode, a metal oxide having electrical conductivity can be mentioned. Specifically, indium oxide, indium-tin oxides (ITO) (including Sn-doped In$_2$O$_3$, crystalline ITO, and amorphous ITO), indium-zinc oxide (IZO) with indium added as a dopant in zinc oxide, indium-gallium oxide (IGO) with indium added as a dopant in gallium oxide, indium-gallium-zinc oxide (IGZO, In—GaZnO$_4$) with indium and gallium added as dopants in zinc oxide, IFO (F-doped In$_2$O$_3$), tin oxide (SnO$_2$), ATO (Sb-doped SnO$_2$), FTO (F-doped SnO$_2$), zinc oxides (including ZnO doped with one or more different elements), aluminum-zinc oxide (AZO) with aluminum added as a dopant in zinc oxide, gallium-zinc oxide (GZO) with gallium added as a dopant in zinc oxide, titanium oxide (TiO$_2$), antimony oxide, spinel-type oxide, and oxides having the YbFe$_2$O$_4$ structure. As an alternative, a transparent electrode containing gallium oxide, titanium oxide, niobium oxide, nickel oxide or the like as a mother layer can be mentioned. As the thickness of the transparent electrode, from $2 \times 10^{-8}$ to $2 \times 10^{-7}$ m, preferably from $3 \times 10^{-8}$ to $1 \times 10^{-7}$ m can be mentioned.

Unless transparency is needed, the conductive material that makes up the cathode having a function as a hole extraction electrode may preferably have a high work function (e.g., $\phi$=4.5 to 5.5 eV). Specific examples may include gold (Au), silver (Ag), chromium (Cr), nickel (Ni), palladium (Pd), platinum (Pt), iron (Fe), iridium (Ir), germanium (Ge), osmium (Os), rhenium (Re), and tellurium (Te). On the other hand, the conductive material that makes up the anode having a function as an electron extraction electrode may preferably have a low work function (e.g., $\phi$=3.5 to 4.5 eV). Specific examples may include alkali metals (e.g., Li, Na, K and the like) and fluorides and oxides thereof, alkaline earth metals (e.g., Mg, Ca and the like) and fluorides and oxides thereof, aluminum (Al), zinc (Zn), tin (Sn), thallium (Tl), sodium-potassium alloys, aluminum-lithium alloys, magnesium-silver alloys, indium, rare earth metals such as ytterbium, and alloys thereof. Examples of the material that makes up the cathode and anode may include metals such as platinum (Pt), gold (Au), palladium (Pd), chromium (Cr), nickel (Ni), aluminum (Al) silver (Ag), tantalum (Ta), tungsten (W), copper (Cu), titanium (Ti), indium (In), tin (Sn), iron (Fe), cobalt (Co), and molybdenum (Mo), and alloys containing one or more of these metal elements, conductive particles made of one or more of these metals, conductive particles of an alloy containing one or more of these metals, and conductive substances such as impurity-doped polysilicons, carbon-based materials, oxide semiconductors, carbon nanotubes, and graphenes. Stacked structures which are each formed of layers each containing one or more of these elements may also be used. Other examples of the material that make up the cathode and anode may include organic materials (conductive polymers) such as poly(3,4-ethylenedioxythiophene)/polystyrene sulfonic acid [PEDOT/PSS]. These conductive materials may each be mixed in a binder (polymer) to prepare a paste or ink composition, which may then be cured to form electrodes to be used.

As a process for forming the first electrode and the second electrode (cathode and anode), a dry process or wet process can be used. Examples of the dry process may include physical vapor deposition (PVD) processes and chemical vapor deposition (CVD) processes. Deposition processes that use the principle of such PVD processes may include vacuum deposition processes using resistance heating or radio-frequency heating, electron beam (EB) deposition processes, various sputtering processes (magnetron sputtering processes, radio frequency-direct current (RF-DC) coupled bias sputtering processes, electron cyclotron resonance (ECR) sputtering processes, facing target sputtering processes, radio-frequency sputtering processes), ion plating processes, laser aberration processes, molecular beam epitaxy processes, and laser transfer processes. CVD processes may include plasma CVD processes, thermal CVD processes, organometallic (MO) CVD processes, and photo-CVD processes. On the other hand, examples of the wet process may include processes such as electrolytic plating processes and electroless plating processes, spin coating processes, inkjet processes, spray coating processes, stamping processes, microcontact printing processes, flexo printing processes, offset printing processes, gravure printing processes, and dipping processes. For patterning, shadow-masking, laser transfer, chemical etching such as photolithography, physical etching by ultraviolet rays or laser beams or the like can be used. As a planarization technique, a laser planarization method, reflow method, chemical mechanical polishing (CMP) method, or the like can be used.

The organic photoelectric conversion layer can take one of the following three structures:
(1) The organic photoelectric conversion layer is formed of a p-type organic semiconductor.

(2) The organic photoelectric conversion layer is formed of a stacked structure of a p-type organic semiconductor layer and an n-type organic semiconductor layer, is formed of a stacked structure of a p-type organic semiconductor layer, a mixed layer (bulk-hetero structure) of a p-type organic semiconductor and an n-type organic semiconductor and an n-type organic semiconductor layer, is formed of a stacked structure of a p-type organic semiconductor layer and a mixed layer (bulk-hetero structure) of a p-type organic semiconductor and an n-type organic semiconductor, or is formed of a stacked structure of an n-type organic semiconductor layer and a mixed layer (bulk-hetero structure) of a p-type organic semiconductor and an n-type organic semiconductor.

(3) The organic photoelectric conversion layer is formed of a mixed layer (bulk-hetero structure) of a p-type organic semiconductor and an n-type organic semiconductor.

Examples of the p-type organic semiconductors may include naphthalene derivatives, anthracene derivatives, phenanthrene derivatives, pyrene derivatives, perylene derivatives, tetracene derivatives, pentacene derivatives, quinacridone derivatives, perylene derivatives, picene derivatives, chrysene derivatives, fluoranthene derivatives, phthalocyanine derivatives, subphthalocyanine derivatives, metal complexes containing heterocyclic compounds as ligands, and the like. Examples of the n-type organic semiconductors may include fullerene and fullerene derivatives, organic semiconductors having greater (deeper) highest occupied molecular orbital (HOMO) and lowest unoccupied molecular orbital (LUMO) than p-type organic semiconductors, and transparent inorganic metal oxides. The n-type organic semiconductors may specifically be heterocyclic compounds containing one or more of nitrogen, oxygen and sulfur atoms. Illustrative are organic molecules, organic metal complexes and subphthalocyanine derivatives having, in parts of molecular frameworks thereof, pyridine, pyrazine, pyrimidine, triazine, quinoline, quinoxaline, isoquinoline, acridine, phenazine, phenanthroline, tetrazole, pyrazole, imidazole, thiazole, oxazole, imidazole, benzimidazole, benzotriazole, benzoxazole, benzoxazole, carbazole, benzofuran, dibenzofuran, or the like. The thickness of the organic photoelectric conversion layer may be, but is not limited to, for example, from $1\times10^{-8}$ to $5\times10^{-7}$ m, preferably from $2.5\times10^{-8}$ to $3\times10^{-7}$ m, more preferably from $2.5\times10^{-8}$ to $2\times10^{-7}$ m, even more preferably from $1\times10^{-7}$ to $1.8\times10^{-7}$ m. Incidentally, organic semiconductors are often classified into p-type and n-type. It is to be noted that the terms "p-type" and "n-type" mean to easily transport holes and to easily transport electrons, respectively, and are not limited to the interpretation of having holes and electrons, as thermally-excited majority carriers unlike as in inorganic semiconductors.

As a process for forming various organic layers, a dry deposition process or wet deposition process can be mentioned. Examples of the dry deposition process may include vacuum deposition processes using resistance heating or radio-frequency heating, EB deposition processes, various sputtering processes (magnetron sputtering processes, RF-DC coupled bias sputtering processes, ECR sputtering processes, facing target sputtering processes, radio-frequency sputtering processes), ion plating processes, laser aberration processes, molecular beam epitaxy processes, and laser transfer processes. Further, CVD processes may include plasma CVD processes, thermal CVD processes, MOCVD processes, and photo-CVD processes. On the other hand, usable examples of the wet deposition process may include processes such as spin coating processes, inkjet processes, spray coating processes, stamping processes, microcontact printing processes, flexo printing processes, offset printing processes, gravure printing processes, and dipping processes. For patterning, shadow-masking, laser transfer, chemical etching such as photolithography, physical etching by ultraviolet rays or laser beams or the like can be used. As a planarization technique, a laser planarization method, reflow method or the like can be used.

Upon depositing the carrier blocking layer, a material having the structural formula (1), (2) or (3) and another organic semiconductor material (e.g., a pentacene derivative) can be co-deposited.

A second carrier blocking layer may be interposed between the organic photoelectric conversion layer and the second electrode (anode). It is to be noted that the carrier blocking layer arranged between the organic photoelectric conversion layer and the first electrode (cathode) may be called "the first carrier blocking layer" for the sake of convenience. The material for use in the second carrier blocking layer (the second carrier blocking material) may preferably be a material having a greater (deeper) ionization potential than the material for use in the first carrier blocking layer. Specific preferred examples are materials, which are organic molecules and organic metal complexes having a heterocycle containing nitrogen (N), such as pyridine, quinoline, acridine, indole, imidazoles, benzimidazole and phenanthroline, in parts of molecular frameworks thereof, and have low light absorption in the visible light region. Further, fullerenes typified by C60 and C70 can also be used if the second carrier blocking layer is formed with a thin film of from $5\times10^{-9}$ to $2\times10^{-8}$ m or so. However, the second carrier blocking layer is not limited to them.

An electron injection layer may also be arranged between the second carrier blocking layer and the second electrode. Examples of a material that forms the electron injection layer may include alkali metals such as lithium (Li), sodium (Na) and potassium (K) and fluorides and oxides thereof, and alkaline earth metals such as magnesium (Mg) and calcium (Ca) and fluorides and oxides thereof.

The image sensor or imaging module may also be provided, as needed, with an on-chip microlens and a light shielding layer, and also with drive circuitries and wirings for driving the image sensor or sensors. A shutter may be arranged, as needed, for controlling the entrance of light into each image sensor, or depending on the purpose of use of the imaging module, an optical cut filter may be arranged. Examples of the array of the image sensors in the imaging module according to the first aspect of the present disclosure may include, in addition to a Bayer array, an interline array, a G-stripe right border (RB) check array, a G-stripe RB complete check array, a check complementary color array, a stripe array, an oblique stripe array, a primary color difference array, a field color difference sequential array, a frame color difference sequential array, a metal oxide semiconductor (MOS) array, an improved MOS array, a frame interleave array, and a field interleave array.

The image sensor of the present disclosure can be formed on a substrate. Here, examples of the substrate may include substrates of organic polymers (polymeric materials in the shapes of flexible plastic films, sheets, plates or the like) exemplified by polymethyl methacrylate (PMMA), polyvinylalcohol (PVA), polyvinylphenol (PVP), polyether sulfone (PES), polyimides, polycarbonates (PC), polyethylene terephthalate (PET), and polyethylene naphthalate (PEN). If a substrate formed from such a flexible polymeric material is used, it is possible to incorporate or integrate the image sensor in or with electronic equipment having, for example, a curved surface shape. Other examples of the substrate may include various glass substrates, various glass substrates with an insulating film formed on surfaces thereof, quartz substrates, quartz substrates with an insulating film formed on surfaces thereof, silicon semiconductor substrates, silicon semiconductor substrates with an insulating film formed on surfaces thereof, and metal substrates made of various alloys and various metals such as stainless steel. Examples of the insulating films may include silicon-oxide-based materials (for example, $SiO_x$ and spin-on-glass (SOG)); silicon nitrides ($SiN_y$); silicon oxynitride (SiON); aluminum oxide ($Al_2O_3$); and metal oxides and metal salts. Conductive substrates with such an insulating film formed on surfaces thereof (substrates made of a metal such as gold or aluminum, and substrates made of highly oriented graphite) may also be used. The surface of the substrate is desirably smooth, but may have such a degree of roughness that does not exert adverse effects on the characteristics of the organic photoelectric conversion layer. The adhesion between the electrode and the substrate may be improved by forming, on the surface of the substrate, a silanol derivative according to the silane-coupling method; forming, on the surface of the substrate, a thin film of a thiol derivative, carboxylic acid derivative, phosphoric acid derivative or the like according to the self-assembled monolayer (SAM) method or the like; or forming, on the surface of the substrate, a thin film of an insulating metal salt or metal complex according to a CVD process or the like.

In some cases, the electrode may be covered with an overlayer. Examples of a material that makes up the overlayer include not only inorganic insulating materials exemplified by high-dielectric metal oxide insulating films, such as silicon oxide-based material; silicon nitrides ($SiN_y$); and aluminum oxide ($Al_2O_3$); but also organic insulating materials (organic polymers) exemplified by polymethyl methacrylate (PMMA); polyvinyl phenol (PVP); polyvinyl alcohol (PVA); polyimides; polycarbonates (PC); polyethylene terephthalate (PET); polystyrene; silanol derivatives (silane coupling agents) such as N-2-(aminoethyl) 3-aminopropyl-trimethoxysilane (AEAPTMS), 3-mercaptopropylt-rimethoxysilane (MPTMS), and octadecyltrichlorosilane (OTS); and straight-chain hydrocarbons having, at one ends thereof, a functional group capable of coupling to the electrode, such as octadecanethiol and dodecyl isocyanate. Two or more of these materials may also be used in combination. Examples of the silicon oxide-based materials may include silicon oxides ($SiO_x$), BPSG, PSG, BSG, AsSG, PbSG, silicon oxynitride (SiON), spin-on-glass (SOG), and low dielectric constant materials (e.g., polyaryl ethers, cycloperfluorocarbon polymers, benzocyclobutene, cyclic fluororesins, polytetrafluoroethylene, fluorinated aryl ethers, fluorinated polyimides, amorphous carbons, and organic SOG). As a process for forming the insulating layer, one of the above-mentioned dry deposition processes and wet deposition processes can be used.

Owing to the formation of the carrier blocking layer with the material having the structural formula (1), (2) or (3), no sensitivity deterioration occurs even when the carrier blocking layer is made thicker. As a reason for this feature, it is considered that thienoacene skeletons as mother skeletons overlap one another in the carrier blocking layer and efficiently transport carriers even when formed into a thick layer. Further, the carrier blocking layer is also excellent in the reduction of a dark current and in dark current vs. voltage characteristics. As reasons for these features, the energy levels of the p-type organic semiconductor of the organic photoelectric conversion layer and the carrier blocking layer, the surface roughness of the thin film upon making thicker the carrier blocking layer formed of the material having the structural formula (1), (2) or (3), stress of the carrier blocking layer, and the like are presumed to bear relevance.

The carrier blocking layer may have a stacked structure of the layer of the material having the structural formula (1), (2) or (3) and another material layer. Specifically, for example, to provide an improved electrical junction, a further material layer may be formed between the carrier blocking layer and the electrode (specifically, the first electrode). The further material layer can be formed of an aromatic amine material represented by a triarylamine compound, benzidine compound or styrylamine compound, a carbazole derivative, a naphthalene derivative, an anthracene derivative, a phenanthrene derivative, a pyrene derivative, a perylene derivative, a tetracene derivative, a pentacene derivative, a perylene derivative, a picene derivative, a chrysene derivative, a fluoranthene derivative, a phthalocyanine derivative, a subphthalocyanine derivative, a hexaazatriphenylene derivative, a metal complex containing a heterocyclic compound as a ligand, poly(3,4-ethylenedioxythiophene)/polystyrene sulfonic acid [PEDOT/PSS], polyaniline, molybdenum oxide ($MoO_x$), ruthenium oxide ($RuO_x$), vanadium oxide ($VO_x$), tungsten oxide ($WO_x$), or the like.

Example 1

Example 1 relates to the image sensors according to the first to third aspects of the present disclosure, and also to the imaging module according to the first aspect of the present disclosure.

Figure 1B:
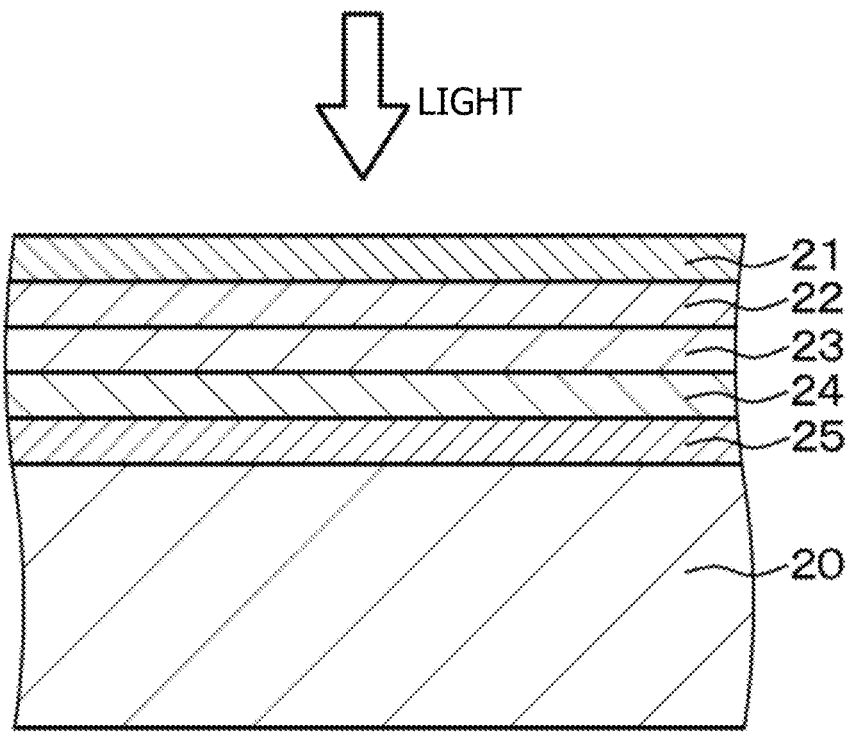

As illustrated in concept diagrams of FIGS. 1A and 1B, each image sensor 11 of Example 1 includes at least a first electrode 21, a second electrode 25, an organic photoelectric conversion layer 23, and a carrier blocking layer 22. Specifically, the first electrode 21 serves as a cathode, the second electrode 25 serves as an anode, and the carrier blocking layer 22 is arranged between the first electrode 21 and the organic photoelectric conversion layer 23. More specifically, each image sensor 11 of Example 1 is formed of at least the first electrode (cathode) 21, the carrier blocking layer (first carrier blocking layer) 22, the organic photoelectric conversion layer 23, and the second electrode (anode) 25 successively stacked one over another. Further, a second carrier blocking layer 24 is also arranged between the organic photoelectric conversion layer 23 and the second electrode 25. The first carrier blocking layer 22 is formed of the above-described material having the structural formula (1), (2) or (3), and has a thickness of from $5 \times 10^{-9}$ to $1.5 \times 10^{-7}$ m, preferably from $5 \times 10^{-9}$ to $1.0 \times 10^{-7}$ m, more preferably from $5 \times 10^{-8}$ to $1.0 \times 10^{-7}$ m. In the image sensor illustrated in FIG. 1A, light enters from the side of the second electrode 25 (the anode side). In the image sensor illustrated in FIG. 1B, on the other hand, light enters from the side of the first electrode 21 (the cathode side). Flows of holes (indicated by "+" in a circle mark) and electrons (indicated by "−" in a circle mark) produced through photoelectric conversion are schematically illustrated in FIG. 2B.

An imaging module 40 of Example 1 includes a plurality of image sensors 11 of Example 1. Specifically, blue image sensors, green image sensors and red image sensors are disposed in a plane as in a Bayer array.

In each image sensor of Example 1, one of the first electrode 21 and the second electrode 25 is formed of a transparent conductive material, and the other electrode is formed of a metal material. In the image sensor illustrated in FIG. 1A, light enters from the side of the second electrode 25 (the anode side). Therefore, the second electrode 25 is formed of a transparent conductive material (e.g., ITO), and the first electrode 21 is formed of Al—Nd (an alloy of aluminum and neodymium) or ASC (an alloy of aluminum, samarium and copper). In the image sensor illustrated in FIG. 1B, on the other hand, light enters from the side of the first electrode 21 (the cathode side). Therefore, the first electrode 21 is formed of a transparent conductive material (e.g., ITO), and the second electrode 25 is formed of Al (aluminum), Al—Si—Cu (an alloy of aluminum, silicon and copper) or Mg—Ag (an alloy of magnesium and silver).

The second carrier blocking layer 24 is formed, for example, of the above-mentioned second carrier blocking material. If the second electrode (anode) is formed of a metal material, the use a material, which contains an element that coordinates the metal in the metal material, is expected to improve the electric junction with the second electrode and hence to decrease the resistant component. Preferred examples may include materials, which do not absorb much light in the visible light region and are organic molecules and organic metal complexes that have, in parts of molecular frameworks thereof, a heterocycle containing nitrogen (N), such as pyridine, quinoline, acridine, indole, imidazole, benzimidazole, or phenanthroline. In the organic photoelectric conversion layer 23 in the blue image sensor provided with the organic photoelectric conversion layer that absorbs blue light (light of from 425 to 495 nm) and has sensitivity to blue color, examples of the p-type organic semiconductor may include naphthalene derivatives, anthracene derivatives, phenanthrene derivatives, pyrene derivatives, tetracene derivatives, picene derivatives, chrysene derivatives, fluoranthene derivatives, metal complexes containing a heterocyclic compound as a ligand, and the like. Examples of the n-type organic semiconductor may include fullerene and fullerene derivatives, organic semiconductors having greater (deeper) HOMO and LUMO than the p-type organic semiconductors, and transparent inorganic metal oxides. As the n-type organic semiconductor, a heterocyclic compound containing one or more of nitrogen, oxygen and sulfur atoms can be exemplified specifically. Illustrative are organic molecules and organic metal complexes having, in parts of molecular frameworks thereof, pyridine, pyrazine, pyrimidine, triazine, quinoline, quinoxaline, isoquinoline, acridine, phenazine, phenanthroline, tetrazole, pyrazole, imidazole, thiazole, oxazole, imidazole, benzimidazole, benzotriazole, benzoxazole, benzoxazole, carbazole, benzofuran, dibenzofuran, or the like. The thickness of the organic photoelectric conversion layer may be, but is not limited to, for example, from $1\times10^{-8}$ to $5\times10^{-7}$ m, preferably from $2.5\times10^{-8}$ to $3\times10^{-7}$ m, more preferably from $2.5\times10^{-8}$ to $2\times10^{-7}$ m, even more preferably from $1\times10^{-7}$ to $1.8\times10^{-7}$ m. In the organic photoelectric conversion layer 23 in the green image sensor provided with the organic photoelectric conversion layer that absorbs green light (light of from 495 to 570 nm) and has sensitivity to green color, examples of the p-type organic semiconductor may include anthracene derivatives, phenanthrene derivatives, pyrene derivatives, perylene derivatives, tetracene derivatives, quinacridone derivatives, fluoranthene derivatives, subphthalocyanine derivatives, metal complexes containing a heterocyclic compound as a ligand, and the like. Examples of the n-type organic semiconductor may include fullerene and fullerene derivatives, organic semiconductors having greater (deeper) HOMO and LUMO than the p-type organic semiconductors, and transparent inorganic metal oxides. The n-type organic semiconductor may specifically be a heterocyclic compound containing one or more of nitrogen, oxygen and sulfur atoms. Illustrative are organic molecules, organic metal complexes and subphthalocyanine derivatives having, in parts of molecular frameworks thereof, pyridine, pyrazine, pyrimidine, triazine, quinoline, quinoxaline, isoquinoline, acridine, phenazine, phenanthroline, tetrazole, pyrazole, imidazole, thiazole, oxazole, imidazole, benzimidazole, benzotriazole, benzoxazole, benzoxazole, carbazole, benzofuran, dibenzofuran, or the like. The thickness of the organic photoelectric conversion layer may be, but is not limited to, for example, from $1\times10^{-8}$ to $5\times10^{-7}$ m, preferably from $2.5\times10^{-8}$ to $3\times10^{-7}$ m, more preferably from $2.5\times10^{-8}$ to $2\times10^{-7}$ m, even more preferably from $1\times10^{-7}$ to $1.8\times10^{-7}$ m. In the organic photoelectric conversion layer 23 in the red image sensor provided with the organic photoelectric conversion layer that absorbs red light (light of from 620 to 750 nm) and has sensitivity to red color, examples of the p-type organic semiconductor may include pentacene derivatives, quinacridone derivatives, perylene derivatives, fluoranthene derivatives, phthalocyanine derivatives, subphthalocyanine derivatives, metal complexes containing a heterocyclic compound as a ligand, and the like. Examples of the n-type organic semiconductor may include fullerene and fullerene derivatives, organic semiconductors having greater (deeper) HOMO and LUMO than the p-type organic semiconductors, and transparent inorganic metal oxides. The n-type organic semiconductor may specifically be a heterocyclic compound containing one or more of nitrogen, oxygen and sulfur atoms. Illustrative are organic molecules, organic metal complexes and subphthalocyanine derivatives having, in parts of molecular frameworks thereof, pyridine, pyrazine, pyrimidine, triazine, quinoline, quinoxaline, isoquinoline, acridine, phenazine, phenanthroline, tetrazole, pyrazole, imidazole, thiazole, oxazole, imidazole, benzimidazole, benzotriazole, benzoxazole, benzoxazole, carbazole, benzofuran, dibenzofuran, or the like. The thickness of the organic photoelectric conversion layer may be, but is not limited to, for example, from $1\times10^{-8}$ to $5\times10^{-7}$ m, preferably from $2.5\times10^{-8}$ to $3\times10^{-7}$ m, more preferably from $2.5\times10^{-8}$ to $2\times10^{-7}$ m.

Figure 2A:
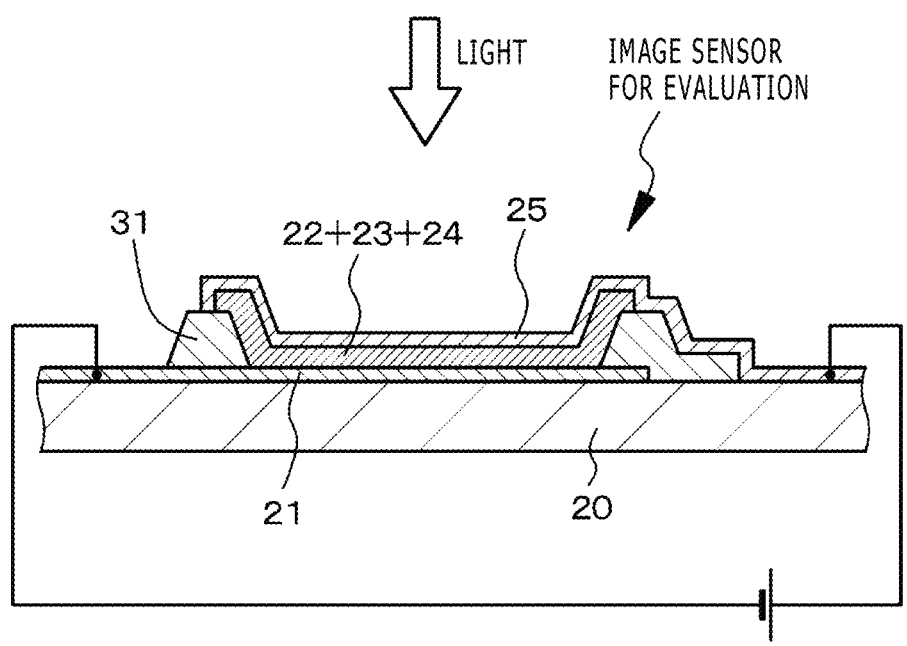
FIGS. 2A and 2B are a schematic, partly cross-sectional view of an image sensor of Example 1 for evaluation and a view schematically illustrating flows of holes and electrons generated through photoelectric conversion.
Figure 2B:
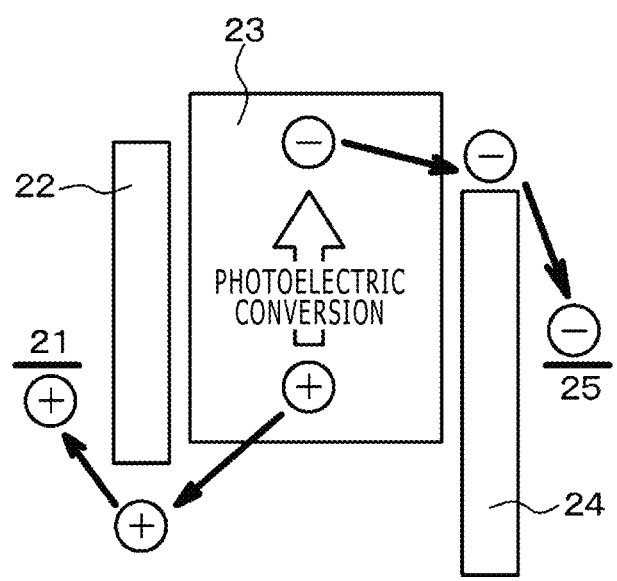

An image sensor for evaluation, a schematic, partly cross-sectional view of which is illustrated in FIG. 2A, was fabricated in a manner to be described below.

On each substrate 20 made of a quartz substrate, an ITO film of 120 nm thickness was deposited using a sputtering system. According to a photolithography technique and an etching technique, a first electrode (cathode) 21 made of the ITO film was obtained. An insulating layer 31 was next formed on the substrate 20 and the first electrode 21. After the insulating layer 31 was subjected to patterning according to the photolithography technique and the etching technique to expose the first electrode 21 of a 1 mm square, ultrasonic cleaning was conducted using a detergent, acetone and ethanol. Subsequent to drying, the substrate was subjected to ultraviolet/ozone treatment for 10 minutes. Then, the substrate 20 was fixed on a substrate holder of a vacuum evaporation system, and a vacuum chamber was depressurized to $5.5\times10^{-5}$ Pa.

Subsequently, based on a vacuum deposition process using a shadow mask, first carrier blocking layers 22 of the material having the structural formula (3) were deposited with five levels of thickness (thickness: 5 nm, 50 nm, 100 nm, 150 nm, 200 nm) on first electrodes 21. In a vacuum evaporation system, quinacridone (QD) and subphthalocyanine chloride (SubPc-Cl) were then co-deposited at a deposition rate ratio of 1:1 to a thickness of 120 nm, whereby organic photoelectric conversion layers 23 were deposited. The organic photoelectric conversion layers 23 were each formed of a mixed layer (bulk-hetero structure) of the p-type organic semiconductor and the n-type organic semiconductor. NBphen was then deposited to a thickness of 5 nm by vacuum evaporation, whereby second carrier blocking layers 24 were formed. Under an inert atmosphere, the resulting substrates were subsequently transferred into another sputtering system, and second electrodes (anodes) 25 of ITO were deposited to a thickness of 60 nm on the second carrier blocking layers 24. Annealing processing was thereafter conducted for two hours and 30 minutes in a nitrogen atmosphere of 150° C., whereby image sensors of Example 1, a schematic, partly cross-sectional view of each of which is illustrated in FIG. 2A were obtained for evaluation.

Comparative Example 1A

Image sensors of Comparative Example 1A were fabricated as in Example 1 except that first carrier blocking layers were deposited with three levels of thickness (thickness: 5 nm, 50 nm, 100 nm) by using the following Compound-A.

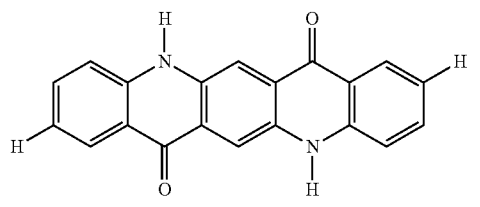

Quinacridone (QD)

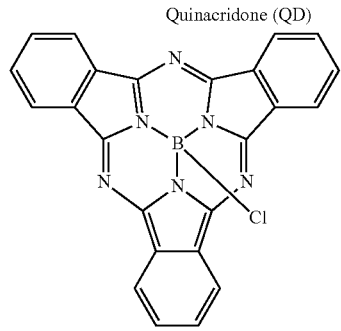

Subphthalocyanine chloride (SubPc-Cl)

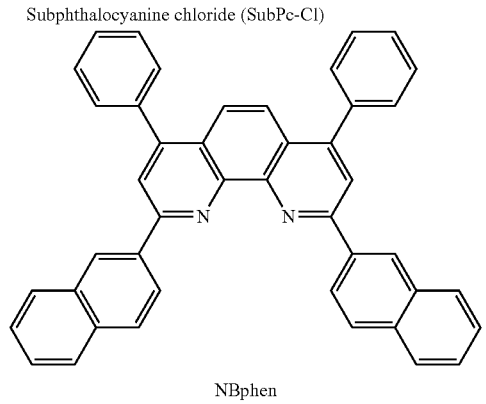

NBphen

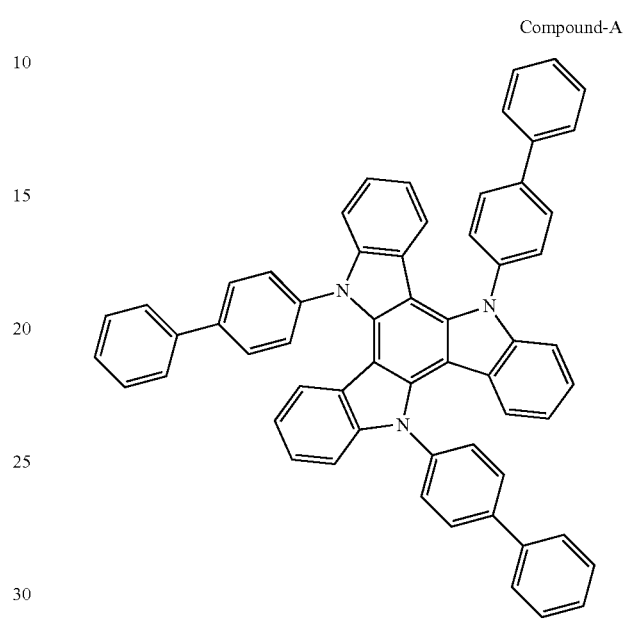

Compound-A

Comparative Example 1B

Image sensors of Comparative Example 1B were fabricated as in Example 1 except that first carrier blocking layers were deposited with three levels of thickness (thickness: 5 nm, 50 nm, 100 nm) by using the following Compound-B.

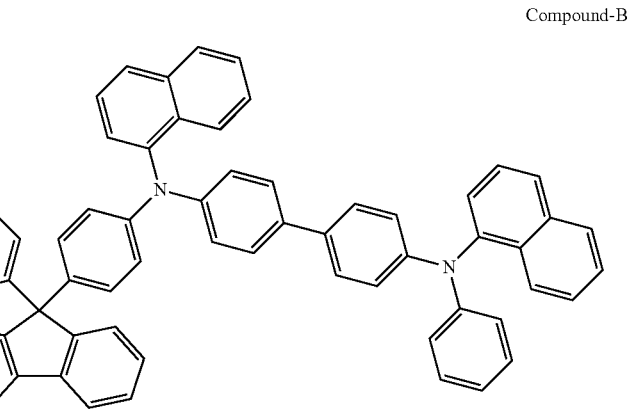

Compound-B

Comparative Example 1C

Image sensors of Comparative Example 1C were fabricated as in Example 1 except that first carrier blocking layers were deposited with three levels of thickness (thickness: 5 nm, 50 nm, 100 nm) by using the following Compound-C.

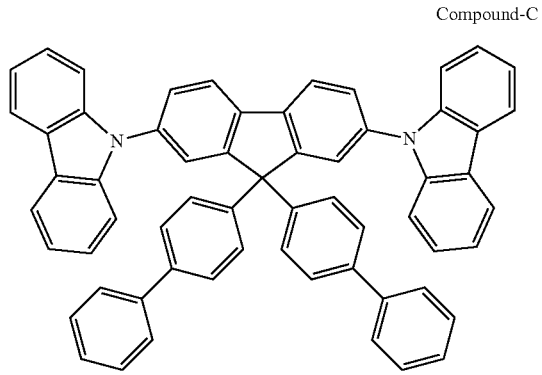 [SMILES: c1ccc(-c2ccc(C3(c4ccc(-c5ccccc5)cc4)c4cc(-n5c6ccccc6c6ccccc65)ccc4-c4ccc(-n5c6ccccc6c6ccccc65)cc43)cc2)cc1]

Compound-C

Figure 4A:
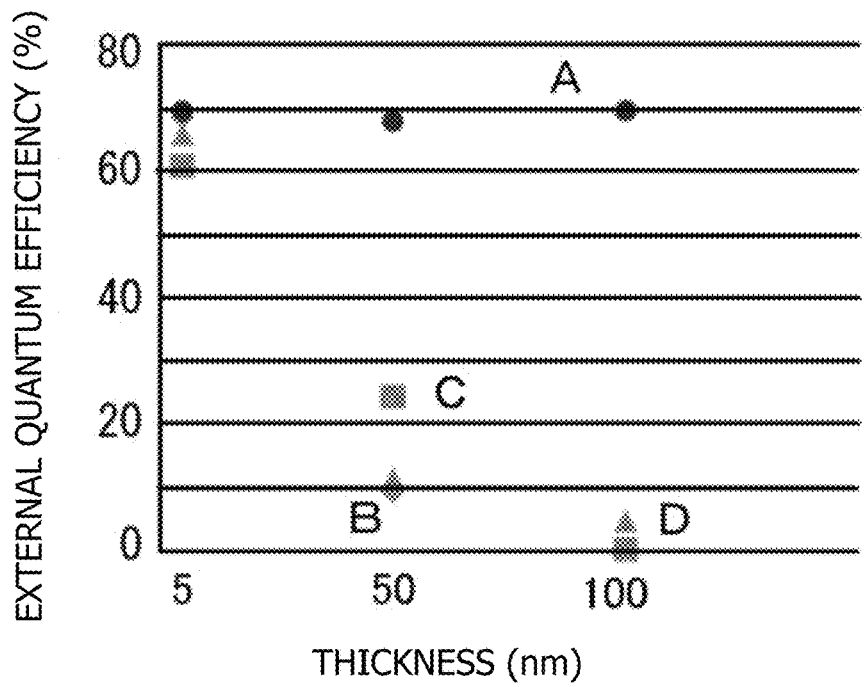
FIG. 4A is a graph representing results of determination of external quantum efficiency when a voltage of −2.6 V is applied between a second electrode and a first electrode while irradiating light of 560 nm wavelength and 2 µW/cm² onto each of image sensors of Example 1 and Comparative Examples 1A, 1B and 1C.
Figure 4B:
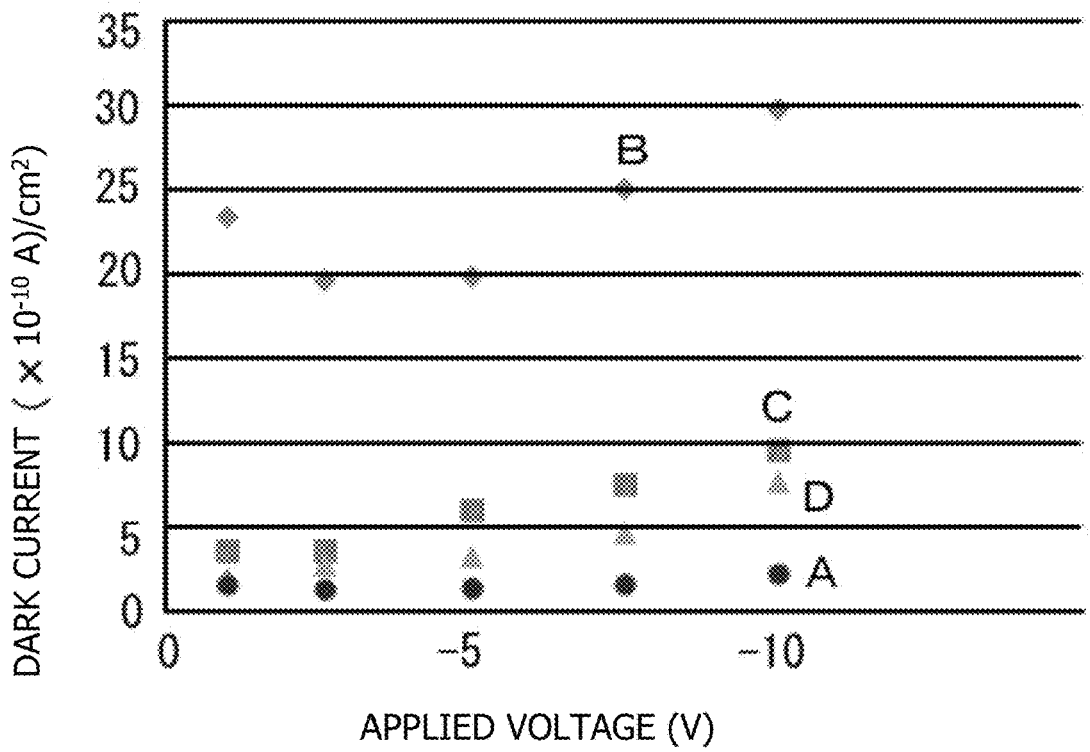
FIG. 4B is a graph representing results of measurement of dark current in a dark place when voltages from −1 to −10 V are applied between the second electrode and the first electrode in each of the image sensors (the thickness of first carrier blocking layer: 100 nm) of Example 1 and Comparative Examples 1A, 1B and 1C.

While irradiating light of 560 nm wavelength at 2 µW/cm$^2$ onto each of the image sensors of Example 1 and Comparative Examples 1A, 1B and 1C, a voltage of −2.6 V (so-called reverse bias voltage: 2.6 V) was applied between the second electrode (anode) and the first electrode (cathode) to determine the external quantum efficiency (EQE). The results are tabulated in Table 1 below and in FIG. 4A. FIG. 4A presents the data at the thickness levels of 5 nm, 50 nm and 100 nm in Example 1 and Comparative Examples 1A, 1B and 1C. In FIG. 4A, the data of Example 1 are indicated by "A," the data of Comparative Example 1A are indicated by "B," the data of Comparative Example 1B are indicated by "C," and the data of Comparative Example 1C are indicated by "D." This applies equally to FIG. 4B to be described subsequently herein.

TABLE 1

|  | Thickness | | | | Unit: % |
| --- | --- | --- | --- | --- | --- |
|  | 5 nm | 50 nm | 100 nm | 150 nm | 200 nm |
| Example 1 | 69.6 | 67.9 | 69.7 | 68.8 | 70.0 |
| Comp. Ex. 1A | 68.7 | 9.3 | 0.2 | | |
| Comp. Ex. 1B | 60.7 | 24.3 | 0.2 | | |
| Comp. Ex. 1C | 65.9 | 11.3 | 4.7 | | |

In Comparative Examples 1A, 1B and 1C in which the aromatic amine compound and the carbazole derivatives useful in organic EL devices and organic thin-film solar cells were used in the first carrier blocking layers, the external quantum efficiency significantly decreased as the thickness of the first carrier blocking layer increased to 50 nm and further to 100 nm, and by a capacity reduction, no improvement can be achieved in the conversion efficiency of an organic module. In the image sensors of Example 1 in which the material having the structural formula (3) was used for the first carrier blocking layer, the external quantum efficiency did not decrease in the range of 5 to 200 nm in the thickness of the first carrier blocking layer, and the thickening of the image sensors has been found to be feasible and to be effective for a reduction in capacity.

In a dark place, a voltage of −2.6 V was applied between the second electrode (anode) and the first electrode (cathode) of each of the image sensors of Example 1 and Comparative Examples 1A, 1B and 1C to measure a dark current. The measurement results are tabulated in Table 2 below. Table 3 indicates the relative values of the dark currents in Comparative Examples 1A, 1B and 1C when the values of the dark currents in Example 1 at the thickness levels of the respective first carrier blocking layers were used as a reference.

TABLE 2

|  | Thickness | | | | Unit: ×10$^{-10}$ A/cm$^2$ |
| --- | --- | --- | --- | --- | --- |
|  | 5 nm | 50 nm | 100 nm | 150 nm | 200 nm |
| Example 1 | 0.871 | 1.05 | 1.18 | 6.74 | 12.4 |
| Comp. Ex. 1A | 1.32 | 5.38 | 19.5 | | |
| Comp. Ex. 1B | 1.55 | 6.37 | 3.47 | | |
| Comp. Ex. 1C | 1.37 | 2.49 | 2.67 | | |

TABLE 3

|  | Thickness | | |
| --- | --- | --- | --- |
|  | 5 nm | 50 nm | 100 nm |
| Example 1 | 1.00 | 1.00 | 1.00 |
| Comp. Ex. 1A | 1.52 | 5.12 | 16.5 |
| Comp. Ex. 1B | 1.78 | 6.08 | 2.93 |
| Comp. Ex. 1C | 1.57 | 2.37 | 2.26 |

From the results of Tables 2 and 3, it is recognized that in Comparative Examples 1A, 1B and 1C, the dark current tends to increase with the thickness of the first carrier blocking layer. Especially at the thickness levels of 50 and 100 nm, dark current values equal to or more than twice as much as those of Example 1 were obtained. In the image sensors of Example 1 in which the material having the structural formula (3) was used as the first carrier blocking layers, on the other hand, the dark current value remained at sufficiently low values although it had a tendency of slightly increasing when the thickness of the first carrier blocking layer was in the range of 5 to 100 nm. As the thickness of the first carrier blocking layer increased to 150 nm and further to 200 nm, however, the dark current value increased. From these results, it has hence been found to be desirable that the thickness of the first carrier blocking layer is from 5 to 150 nm, preferably from 5 to 100 nm. It has not been ascertained why the dark current value increases when the thickness increases to a certain extent or further. This is, however, believed to be attributable to changes or the like in the state of the interface between the first carrier blocking layer and the organic photoelectric conversion layer due to an increase in the roughness of the surface of the first carrier blocking layer and a change of stress in the first carrier blocking layer, both of which were caused by the thickening of the first carrier blocking layer. From the above results, with the thickness of the first carrier blocking layer in the range of 5 to 150 nm, the use of the material of the structural formula (3) in the first carrier blocking layer can provide a large S/N ratio, whereby the provision of an image sensor suited for a reduced capacity is feasible.

Further, the dark current was measured in a dark place by applying voltages from −1 to −10 V (so-called reverse bias voltage: 1 to 10 V) between the second electrode (anode) and the first electrode (cathode) of each image sensor in which the thickness of the first carrier blocking layer was set at 100 nm. The measurement results are tabulated in Table 4, and are presented as a graph in FIG. 4B.

TABLE 4

| | \multicolumn{5}{c}{Unit: ×10⁻¹⁰ A/cm²} |
| | Voltage | | | | |
| | −1.0 V | −2.6 V | −5.0 V | −7.5 V | −10 V |
|---|---|---|---|---|---|
| Example 1 | 1.46 | 1.18 | 1.25 | 1.47 | 2.10 |
| Comp. Ex. 1A | 23.3 | 19.5 | 19.8 | 25.0 | 29.7 |
| Comp. Ex. 1B | 3.45 | 3.47 | 5.92 | 7.45 | 9.46 |
| Comp. Ex. 1C | 1.88 | 2.67 | 3.16 | 4.55 | 7.60 |

It is understood that compared with Comparative Examples 1A, 1B and 1C, Example 1 indicates smaller increments in dark current even when the absolute value of the applied voltage increases, and dark current vs. voltage characteristics is excellent. In other words, it is understood that the use of the material of the structural formula (3) in the first carrier blocking layer can provide not only a large S/N ratio but also excellent dark current vs. voltage characteristics that enable high-voltage drive of the resulting image sensor.

The first carrier blocking layer is required not only to have the electrical characteristics but also not to absorb, if at all possible, light in the visible light region so that, even when thickened, the first carrier blocking layer does not interfere with photoelectric conversion in the organic photoelectric conversion layer or inorganic photoelectric conversion layer forming another image sensor located below. As mentioned above, many of organic compounds generally have a high absorption intensity in the region of wavelengths on the side shorter than 450 nm, and hence involve the problem of absorbing blue light that is supposed to be absorbed in the organic photoelectric conversion layer of the image sensor. Accordingly, for a spectral simulation, the light absorbance of a carrier blocking layer has been calculated to preferably be 3% or less at 450 nm wavelength, 30% or less at 425 nm wavelength, and 80% or less at 400 nm wavelength.

Figure 5:
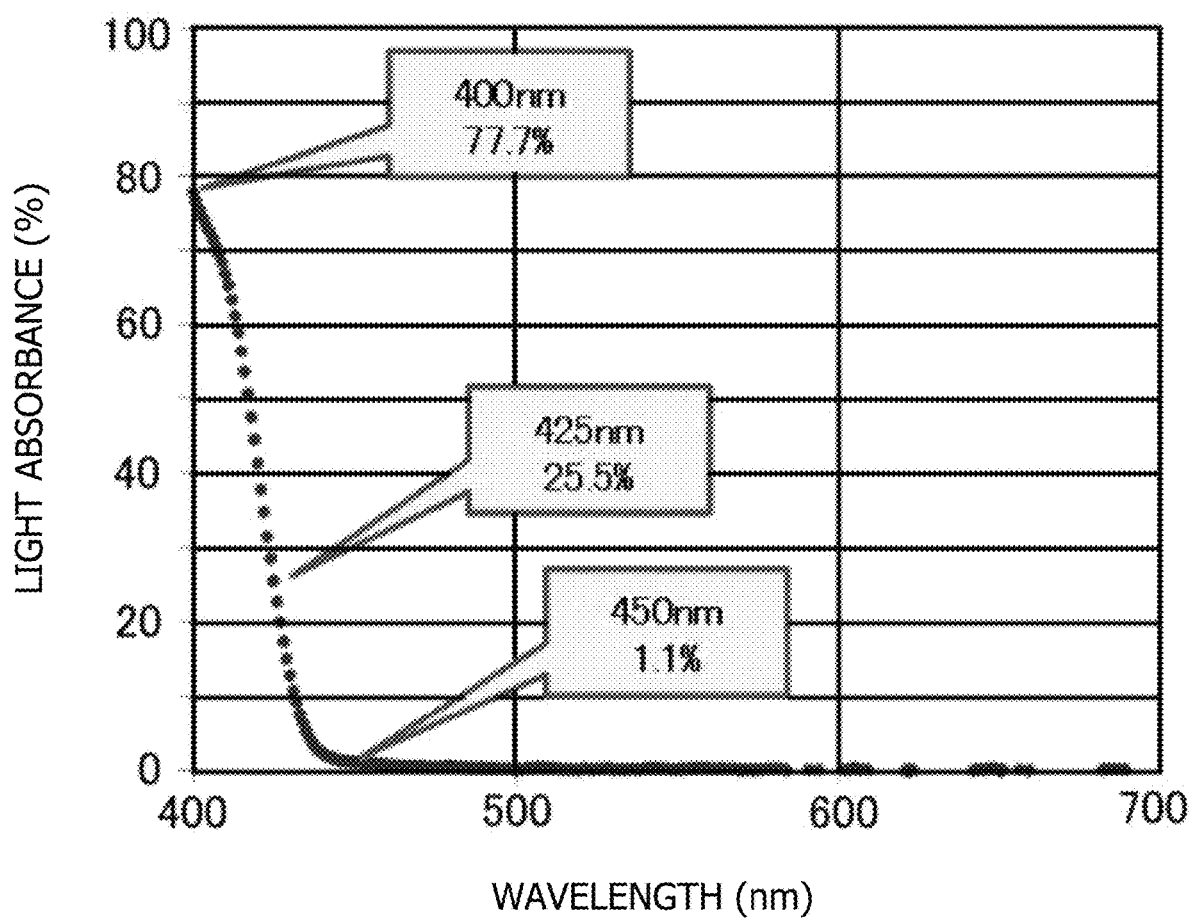
FIG. 5 is a diagram representing results of determination of the light absorption spectrum (light absorbance) of a thin film made from the material having the structural formula (3).

Spectral measurement was conducted to measure the absorption of light in the visible light region when the material having the structural formula (3) was formed thinner. Specifically, a thin film was formed on a quartz substrate to a thickness of 50 nm from the material of the structural formula (3) based on a vacuum deposition process, and its light absorption spectrum (light absorbance) in the case of the thickness of 150 nm as calculated by light transmittance measurement and light reflectivity measurement was determined. The results are presented in FIG. 5. It has been found that the light absorbance of the material having the structural formula (3) is 1.1% at 450 nm, 25.5% at 425 nm, and 77.7% at 400 nm and can hence achieve the target values of light absorbance at the three wavelengths. In short, it is also understood from spectral characteristics that the material having the structural formula (3) allows thickening up to 150 nm. In other words, it has been found that the material having the structural formula (3) has excellent light absorption characteristics and does not interfere with the photoelectric conversion function of the image sensor.

Figure 3:
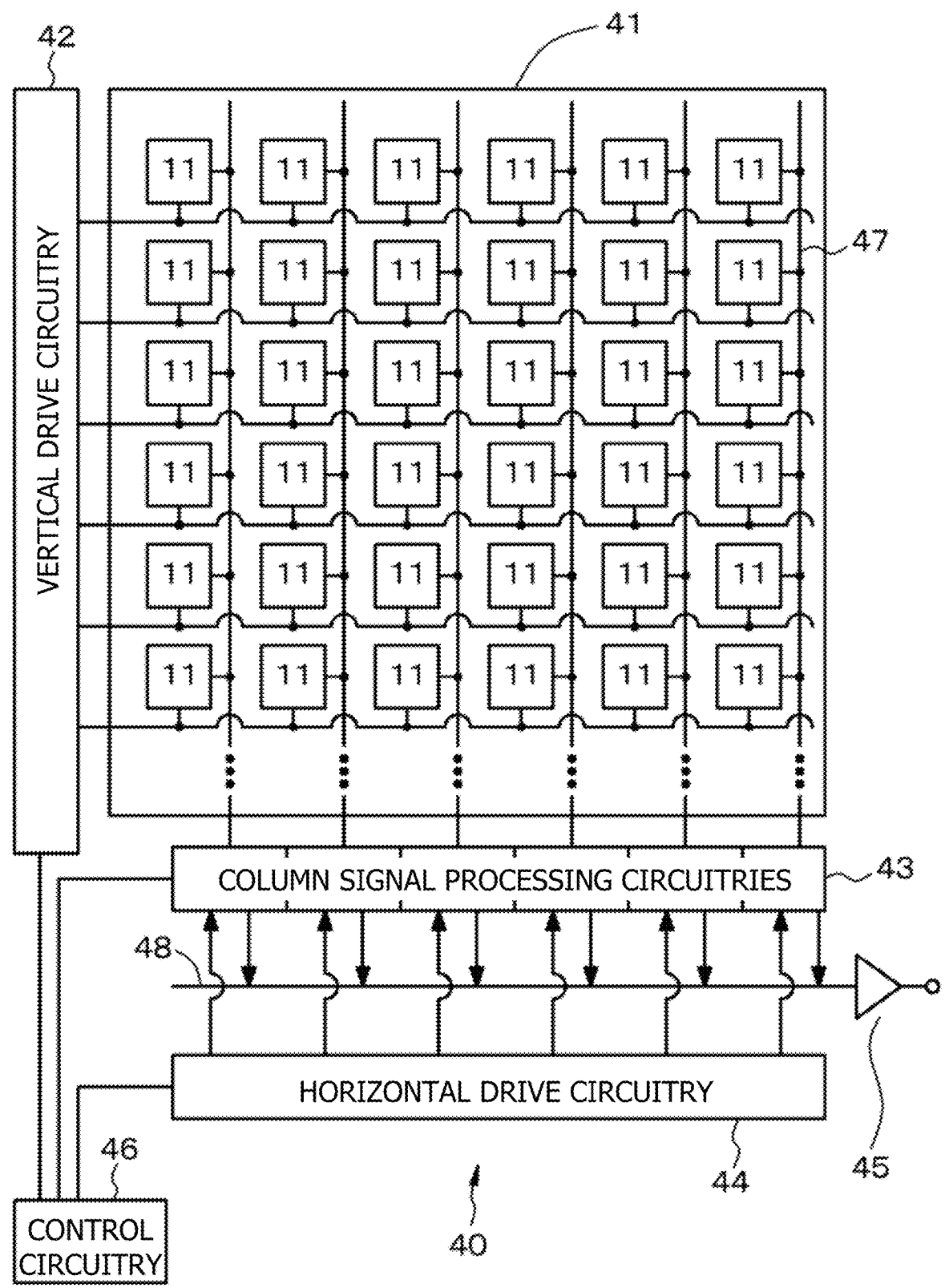
FIG. 3 is a concept diagram of an imaging module of Example 1.

FIG. 3 is a concept diagram of the imaging module of Example 1. The imaging module 40 of Example 1 includes, on a semiconductor substrate (e.g., a silicon semiconductor substrate), an imaging region 41 having a plurality of the image sensors 11 described above and disposed in a two-dimensional array pattern, and as peripheral circuitries therefor, a vertical drive circuitry 42, column signal processing circuitries 43, a horizontal drive circuitry 44, an output circuitry 45, a control circuitry 46, and the like. Obviously, these circuitries may be formed from well-known circuitries or may be formed using other circuitry configurations (for example, various circuitries used in conventional charge-coupled device (CCD) or complementary metal oxide semiconductor (CMOS) imaging modules).

The control circuitry 46 generates clock signals and control signals as a reference for the operation of the vertical drive circuitry 42, the column signal processing circuitries 43, and the horizontal drive circuitry 44 based on vertical synchronizing signals, horizontal synchronizing signals, and master clock. The generated clock signals and control signals are inputted to the vertical drive circuitry 42, the column signal processing circuitries 43 and the horizontal drive circuitry 44.

The vertical drive circuitry 42 is configured, for example, of a shift register, and sequentially selects and scans the respective image sensors 11 in the imaging region 41 row by row in the vertical direction. A pixel signal based on a current (signal) produced depending on the quantity of light received at each image sensor 11 is sent to the corresponding column signal processing circuitry 43 via an associated vertical signal line 47.

The column signal processing circuitries 43 are arranged, for example, for the columns of the image sensors 11, and perform signal processing of signals, which have been outputted from the image sensors 11 in each row, for each image sensor, for noise removal or signal amplification by signals from black reference pixels (which are formed around an effective pixel region although not illustrated). Horizontal selection switches (not illustrated) are arranged at output stages of the column signal processing circuitries 43, and are connected between a horizontal signal line 48 and the column signal processing circuitries 43.

The horizontal drive circuitry 44 is configured, for example, of a shift register, sequentially outputs horizontal scanning pulses to select the column signal processing circuitries 43 one after another, and outputs signals from the respective column signal processing circuitries 43 to the horizontal signal line 48.

The output circuitry 45 performs signal processing on signals sequentially supplied from the respective column signal processing circuitries 43 via the horizontal signal line 48, and outputs the processed signals.

As the organic photoelectric conversion layer itself functions as a color filter, color separation is possible without any arrangement of the color filter.

As has been described above, in each image sensor of Example 1, the carrier blocking layer arranged between the organic photoelectric conversion layer and the first electrode is formed of the material having the structural formula (1), (2) or (3) that does not absorb much visible light. Therefore, the carrier blocking layer does not interfere with photoelectric conversion in the image sensor including the carrier blocking layer or the image sensor located as a lower layer as viewed in the direction of incident light, and can achieve both good external quantum efficiency and spectral characteristics. Moreover, the carrier blocking layer can suppress a dark current, and can improve dark current vs. voltage characteristics. Hence, the carrier blocking layer functions as a carrier transport layer for a photocurrent, while it also functions as a carrier blocking layer for a dark current. In addition, the setting of the thickness of the carrier blocking layer at from 5 to 150 nm, preferably from 5 to 100 nm enables a reduction in electric capacity as a problem of conventional image sensors, and can also assure good spectral characteristics at the same time. As a consequence of the foregoing, it is possible to realize an imaging module that enables beautiful imaging.

Example 2

Example 2 is a modification of Example 1. In Example 2, similar to Example 1, based on the vacuum deposition process using the shadow mask, first carrier blocking layers 22 of the material having the structural formula (3) were deposited to a thickness of 5 nm on first electrodes 21. Different from Example 1, 2,9-dimethylquinacridone (see the structural formula below) and subphthalocyanine chloride (SubPc-Cl) were then co-deposited at a deposition rate

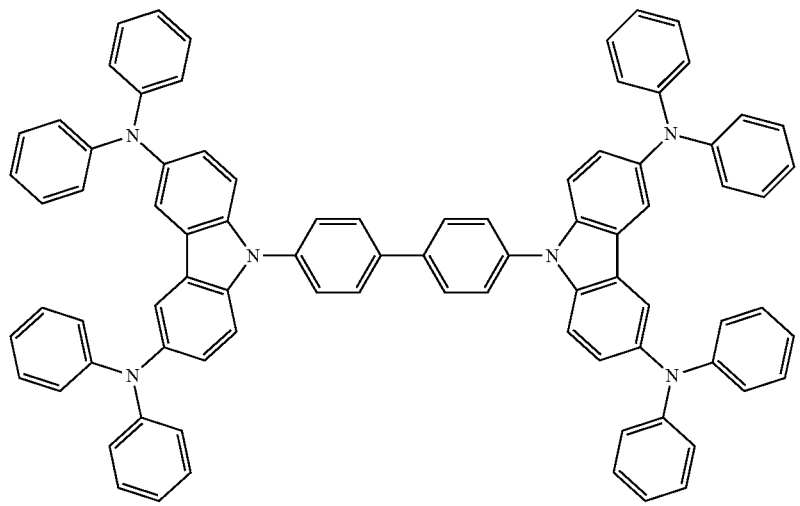

ratio of 1:1 to a thickness of 120 nm in the vacuum evaporation system, whereby organic photoelectric conversion layers 23 were deposited. The organic photoelectric conversion layers 23 were each formed of a mixed layer (bulk-hetero structure) of the p-type organic semiconductor and the n-type organic semiconductor. Subsequently, following the procedures of Example 1, image sensors of Example 2 were obtained for evaluation. The image sensors of Example 2 for evaluation had a cross-sectional structure similar to that illustrated in FIG. 2A.

2,9-Dimethylquinacridone

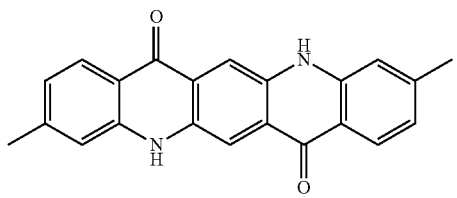

Comparative Example 2B

Image sensors of Comparative Example 2B were fabricated as in Example 2 except that first carrier blocking layers were deposited to a thickness of 5 nm by using the above-described Compound-B.

Comparative Example 2C

Image sensors of Comparative Example 2C were fabricated as in Example 2 except that first carrier blocking layers were deposited to a thickness of 5 nm by using the above-described Compound-C.

Comparative Example 2D

Image sensors of Comparative Example 2D were fabricated as in Example 2 except that first carrier blocking layers were deposited to a thickness of 5 nm by using the below-described Compound-D.

While applying −3 V (so-called reverse bias voltage: 3 V) between the second electrode (anode) 25 and the first electrode (cathode) 21 in each of the image sensors of Example 2 and Comparative Examples 2B, 2C and 2D, light of 560 nm wavelength was irradiated at 2 μW/cm². The irradiation of light was next stopped (specifically, a shutter was closed). The value (unit: millisecond) of $T_0$ was then measured, where $T_0$ was a time from the stop of the irradiation of light until a quantity of current decreased to $0.03 \times I_0$ ($I_0$: quantity of current flowing between the second electrode and the first electrode immediately before the stop of the irradiation of light), that is, to 3% to the value of $I_0$. The measurement results are tabulated in Table 5 below. It is to be noted that in Table 5, the "residual image ratio" is the relative value of each Comparative Example when the value of $T_0$ in Example 2 is assumed to be "1."

TABLE 5

|  | $T_0$ | Residual image ratio |
|---|---|---|
| Example 2 | 8 | 1.0 |
| Comp. Ex. 2B | 28 | 3.4 |
| Comp. Ex. 2C | 27 | 3.3 |
| Comp. Ex. 2D | 30 | 3.7 |

From Table 5, it has been found that the residual image time of each of Comparative Examples 2B, 2C and 2D is equal to or more than thrice as much as that of Example 2 and that the use of the material having the structural formula (3) in the first carrier blocking layer provides excellent residual image characteristics. As presented in Table 6, as the external quantum efficiency (EQE) upon application of a reverse bias voltage of 3 V, Example 2 also indicates a better value. Consequently, the material having the structural formula (3) can improve residual image characteristics while assuring good sensitivity.

TABLE 6

|  | External quantum efficiency |
| --- | --- |
| Example 2 | 57.0% |
| Comp. Ex. 2B | 56.7% |
| Comp. Ex. 2C | 54.7% |
| Comp. Ex. 2D | 56.4% |

Table 7 presents values of external quantum efficiency (EQE) and $T_0$ (unit: millisecond) when the first carrier blocking layer of the material having the structural formula (3) was changed to 5 nm, 50 nm and 100 nm in thickness. From Table 7, it is understood that no substantial change occurs in residual image time $T_0$ up to 100 nm of the thickness of the first carrier blocking layer and that the use of the material having the structural formula (3) as the first carrier blocking layer can assure a desired electric capacity in addition to improvements in residual image characteristics and an improvement in quantum efficiency.

TABLE 7

| Thickness of the first carrier blocking layer in Example 1 | EQE | $T_0$ |
| --- | --- | --- |
| 5 nm | 69.6% | 8 |
| 50 nm | 67.9% | 4 |
| 100 nm | 69.7% | 6 |

Further, stacked structures for testing were each fabricated to a thickness of 200 nm with a first carrier blocking layer of the material having the structural formula (3) between a first electrode (specifically, a first electrode having a stacked structure of 100 nm thick platinum/0.8 nm thick molybdenum oxide) and a second electrode (specifically, a second electrode having a stacked structure of 3 nm thick molybdenum oxide/100 nm thick gold). Voltages of from −1 to −10 V (so-called reverse bias voltage: 1 to 10 V) were each applied between the second electrode (anode) and the first electrode (cathode) to determine carrier mobility (unit: ×10$^{-2}$ cm$^2$/V·s). The results are tabulated in Table 8 below. The carrier mobility did not have dependence on the value of the reverse bias voltage, and moreover, was higher by three orders of magnitude or so compared with aromatic amine materials and carbazole materials.

TABLE 8

| Reverse bias voltage | Carrier mobility |
| --- | --- |
| 1 V | 6.07 |
| 3 V | 6.23 |
| 5 V | 6.33 |
| 10 V | 6.53 |

Figure 6:
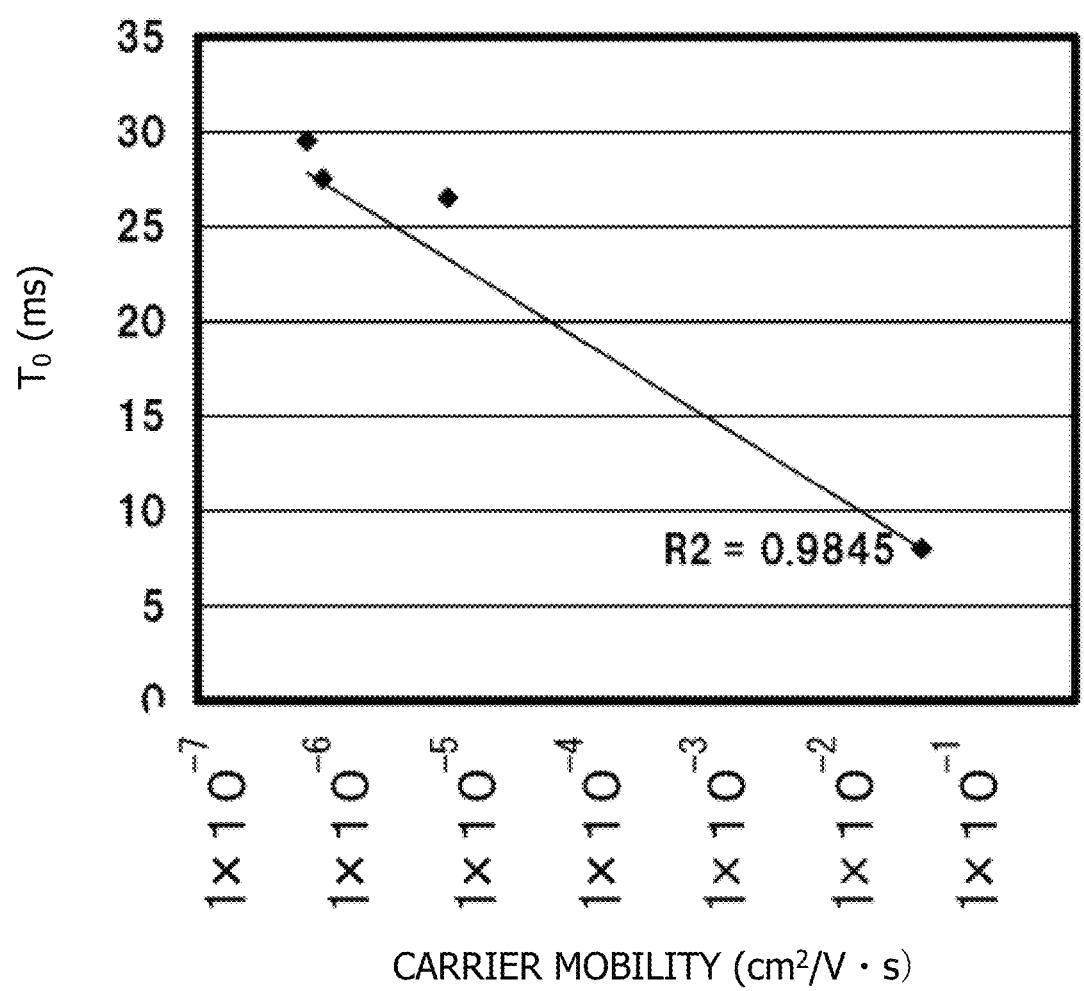
FIG. 6 is a diagram representing a relationship of carrier mobility vs. the value of $T_0$ in Example 2.

Further, stacked structures for testing were fabricated to a thickness of 200 nm with first carrier blocking layers, which were formed of the material having the structural formula (3) and aromatic amine materials (A), (B) and (C), between first electrodes (specifically, first electrodes having a stacked structure of 100 nm thick platinum/0.8 nm thick molybdenum oxide) and second electrodes (specifically, second electrodes having a stacked structure of 3 nm thick molybdenum oxide/100 nm thick gold). A voltage of −1 V (so-called reverse bias voltage: 1 V) was applied between each second electrode (anode) and the associated first electrode (cathode) to determine carrier mobility (unit: cm$^2$/V·s). The results are tabulated in Table 9 below, together with values (unit: millisecond) of $T_0$ in image sensors that used these materials as 5 nm thick first carrier blocking layers. In addition, correlations between carrier mobility and the value of $T_0$ are presented in FIG. 6.

TABLE 9

|  | Carrier mobility | $T_0$ |
| --- | --- | --- |
| Structural formula (3) | 6.07 × 10$^{-2}$ | 8 |
| Aromatic amine material (A) | 1.00 × 10$^{-6}$ | 28 |
| Aromatic amine material (B) | 7.43 × 10$^{-7}$ | 30 |
| Aromatic amine material (C) | 1.00 × 10$^{-5}$ | 27 |

From Table 9, the material having the structural formula (3) indicated carrier mobility higher by three orders of magnitude or so compared with the aromatic amine materials. It is also understood that the material having the structural formula (3) is also far better in residual image characteristics.

Example 3

Figure 7A:
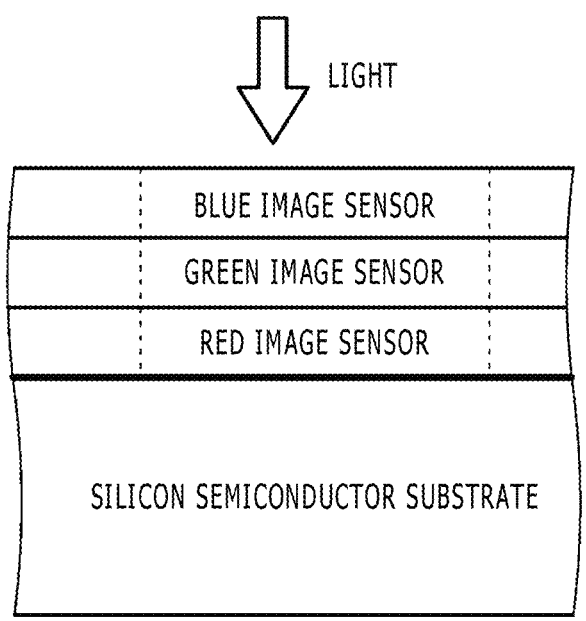
FIGS. 7A and 7B are concept diagrams of stacked imaging devices of Example 3.

Example 3 is modifications of the image sensors of Examples 1 and 2, and relates to a stacked imaging device of the present disclosure and the imaging module according to the second aspect of the present disclosure. Described specifically, the stacked imaging device (vertically spectral imaging device) of Example 3 is formed of at least two image sensors, which are the same as one of the image sensors described in Examples 1 and 2, stacked one over the other. On the other hand, the imaging module of Example 3 includes a plurality of such stacked imaging devices. Specifically, the stacked imaging device of Example 3 has, as illustrated in a concept diagram of FIG. 7A, a configuration that three image sensors (three subpixels) consisting of the blue image sensor, the green image sensor and the red image sensor described in Examples 1 and 2 are stacked in a vertical direction. A stacked imaging device having the structure that subpixels are stacked to form a single pixel can be obtained accordingly. The blue image sensor is located as the top layer, the green image sensor is located at the middle, and the red image sensor is located as the bottom layer. However, the order of stacking shall not be limited to this configuration.

Figure 7B:
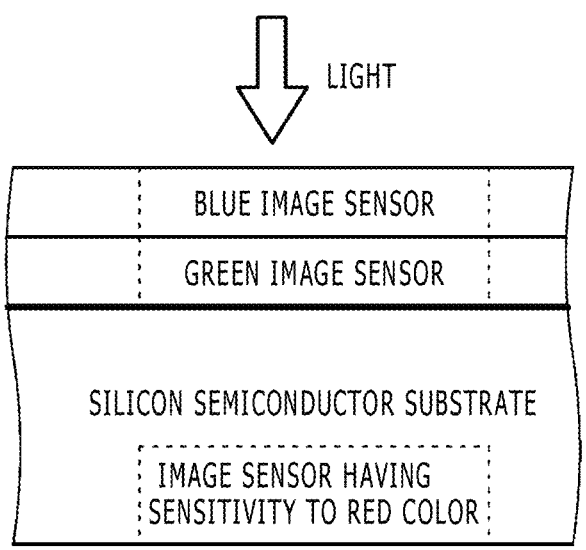

As an alternative, as illustrated in a concept diagram of FIG. 7B, a stacked imaging device can be obtained with a stacked structure of image sensors by arranging two of the image sensors described in Examples 1 and 2 (a blue image sensor and a green image sensor in the illustrated example) on a silicon semiconductor substrate and arranging one or more image sensors (an image sensor having sensitivity to red color in the illustrated example) inside the silicon semiconductor substrate located below the two image sensors, in short, with a structure that subpixels are stacked to form a single pixel. The image sensors formed on and in the silicon semiconductor substrate may preferably be of the back-illuminated type, but may be provided as the front-illuminated type. Instead of arranging a photoelectric conversion layer inside the silicon semiconductor substrate, an image sensor may be formed on the semiconductor substrate by an epitaxial growth process, or may be formed in a silicon layer in a so-called silicon on insulator (SOI) structure.

In each stacked imaging device of Example 3, to avoid interfering with the reception of light by the image sensor or image sensors located below, the first electrode (cathode) and the second electrode (anode) in each image sensor located above are both formed from a transparent conductive material such as, for example, ITO.

In the imaging module of Example 3 which was provided with the plurality of the stacked imaging devices, instead of performing the spectroscopy of blue color, green color and red color through color filters, image sensors having sensitivity to light of plural ranges of wavelengths are stacked in the direction of incident light in the same pixel, thereby making it possible to improve the sensitivity and also the pixel density per unit volume. As an organic material has a high absorption coefficient, an organic photoelectric conversion layer can be made thinner compared with conventional Si-based photoelectric conversion layers, thereby reducing the leakage of light from adjacent pixels and relaxing the restriction to the incident angle of light. Further, conventional Si-based image sensors produce false colors due to the generation of color signals by performing interpolation processing among the pixels of the three colors. With the imaging module of Example 3 provided with the plurality of stacked imaging devices, the production of false colors is suppressed.

The present disclosure has been described based on the preferred Examples, but the present disclosure shall not be limited to these Examples. The structures, configurations, fabrication conditions, fabrication processes, and materials used of/for the image sensors, stacked imaging devices and imaging modules described in the Examples are merely illustrative, and can be changed appropriately.

Defining an image sensor from the standpoints of external quantum efficiency and the thickness of a carrier blocking layer, the image sensor of the present disclosure includes at least a first electrode, a second electrode, an organic photoelectric conversion layer, and a carrier blocking layer, the carrier blocking layer has a thickness of from $5\times10^{-9}$ to $1.0\times10^{-7}$ m, preferably from $5\times10^{-8}$ to $1.5\times10^{-7}$ m, and the value of external quantum efficiency (EQE) may be 0.6 or greater when a voltage of −2.6 V (so-called reverse bias voltage: 2.6 V) is applied between the second electrode (anode) and the first electrode (cathode) while irradiating light of 560 nm wavelength at 2 μW/cm$^2$.

As an alternative, defining an image sensor from the standpoints of dark current and the thickness of a carrier blocking layer, the image sensor of the present disclosure includes at least a first electrode, a second electrode, an organic photoelectric conversion layer, and a carrier blocking layer, the carrier blocking layer has a thickness of from $5\times10^{-9}$ to $1.0\times10^{-7}$ m, preferably from $5\times10^{-8}$ to $1.0\times10^{-7}$ m, and the value of a dark current may be $2.5\times10^{-10}$ A/cm$^2$ or smaller when voltages of from −1 to −10 V (so-called reverse bias voltage: 1 to 10 V) are applied between the second electrode (anode) and the first electrode (cathode).

As a further alternative, defining an image sensor from the standpoints of residual image characteristics and the thickness of a carrier blocking layer, the image sensor of the present disclosure includes at least a first electrode, a second electrode, an organic photoelectric conversion layer, and a carrier blocking layer, the carrier blocking layer has a thickness of from $5\times10^{-9}$ to $1.0\times10^{-7}$ m, preferably from $5\times10^{-8}$ to $1.0\times10^{-7}$ m, and when light of 560 nm wavelength is irradiated at 2 μW/cm$^2$ while applying −3 V (so-called reverse bias voltage: 3 V) between the second electrode and the first electrode and the irradiation of light is then stopped, $T_0$ may be 10 milliseconds or less where $T_0$ is a time from the stop of the irradiation of light until a quantity of current decreases to $0.03\times I_0$ ($I_0$: quantity of current flowing between the second electrode and the first electrode immediately before the stop of the irradiation of light).

As a still further alternative, defining an image sensor from the standpoints of light absorbance and the thickness of a carrier blocking layer, the image sensor of the present disclosure includes at least a first electrode, a second electrode, an organic photoelectric conversion layer, and a carrier blocking layer, the carrier blocking layer has a thickness of from $5\times10^{-9}$ to $1.0\times10^{-7}$ m, preferably from $5\times10^{-8}$ to $1.0\times10^{-7}$ m, and the carrier blocking layer may have a light absorbance of 3% or less at 450 nm wavelength, 30% or less at 425 nm wavelength, and 80% or less at 400 nm wavelength.

As an even further alternative, defining an image sensor from the standpoints of carrier mobility and the thickness of a carrier blocking layer, the image sensor of the present disclosure includes at least a first electrode, a second electrode, an organic photoelectric conversion layer, and a carrier blocking layer, the carrier blocking layer has a thickness of from $5\times10^{-9}$ to $1.0\times10^{-7}$ m, preferably from $5\times10^{-8}$ to $1.0\times10^{-7}$ m, and the carrier blocking layer is formed of a material having a carrier mobility of $9\times10^{-4}$ cm$^2$/V·s or higher, preferably $9\times10^{-3}$ cm$^2$/V·s or higher, more preferably $6\times10^{-2}$ cm$^2$/V·s or higher.

The present disclosure can also have the following configurations.

[A01] Image Sensor: First Aspect

An image sensor including at least:
a first electrode;
a second electrode;
an organic photoelectric conversion layer; and
a carrier blocking layer,
in which the carrier blocking layer is formed of a material having the following structural formula (1), and has a thickness of from $5\times10^{-9}$ to $1.5\times10^{-7}$ m, preferably from $5\times10^{-9}$ to $1.0\times10^{-7}$ m:

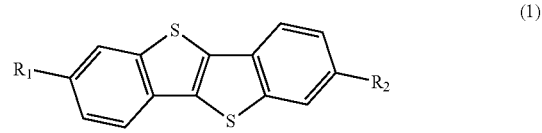

(1)

wherein $R_1$ and $R_2$ are independently a group selected from H, an aryl group and an alkyl group,
the aryl group is a group selected from the group consisting of phenyl, biphenyl, terphenyl, naphthyl, naphthylphenyl, tolyl, xylyl, C2-C6 alkyl-substituted phenyl, anthracenyl, anthracenylphenyl, phenanthryl, phenanthrylphenyl, pyrenyl, pyrenylphenyl, tetracenyl, tetracenylphenyl, fluoranthenyl, fluoranthenylphenyl, pyridinyl, pyridinylphenyl, quinolinyl, quinolylphenyl, acridinyl, acridinylphenyl, indol, indolylphenyl, imidazol, imidazolylphenyl, benzimidazole, benzimidazolylphenyl, thienyl, and thienyelphenyl, and the alkyl group is a group selected from the group consisting of methyl, ethyl, propyl, butyl, pentyl, and hexyl, which is a straight-chain alkyl group or a branched alkyl group.

[A02] Image Sensor: Second Aspect

An image sensor including at least:
a first electrode;
a second electrode;

an organic photoelectric conversion layer; and
a carrier blocking layer,
in which the carrier blocking layer is formed of a material having the following structural formula (2), and has a thickness of from $5\times10^{-9}$ to $1.5\times10^{-7}$ m, preferably from $5\times10^{-9}$ to $1.0\times10^{-7}$ m:

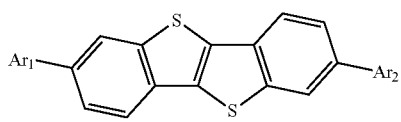

(2)

wherein $Ar_1$ and $Ar_2$ are independently a substituted or unsubstituted aryl group, which is selected from the group consisting of phenyl, biphenyl, terphenyl, naphthyl, naphthylphenyl, tolyl, xylyl, C2-C6 alkyl-substituted phenyl, anthracenyl, anthracenylphenyl, phenanthryl, phenanthrylphenyl, pyrenyl, pyrenylphenyl, tetracenyl, tetracenylphenyl, fluoranthenyl, fluoranthenylphenyl, pyridinyl, pyridinylphenyl, quinolinyl, quinolylphenyl, acridinyl, acridinylphenyl, indol, indolylphenyl, imidazol, imidazolylphenyl, benzimidazole, benzimidazolylphenyl, thienyl, and thienyelphenyl.

[A03] Image Sensor: Third Aspect
An image sensor including at least:
a first electrode;
a second electrode;
an organic photoelectric conversion layer; and a carrier blocking layer,
in which the carrier blocking layer is formed of a material having the following structural formula (3), and has a thickness of from $5\times10^{-9}$ to $1.5\times10^{-7}$ m, preferably from $5\times10^{-9}$ to $1.0\times10^{-7}$ m:

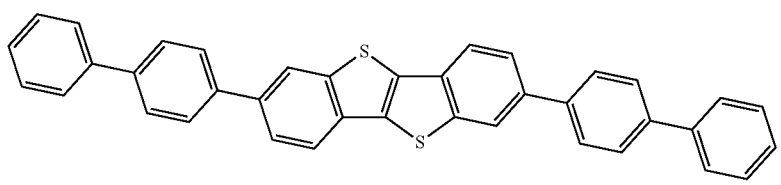

(3)

[A04]
An image sensor including at least:
a first electrode;
a second electrode;
an organic photoelectric conversion layer; and
a carrier blocking layer,
in which the carrier blocking layer has a thickness of from $5\times10^{-9}$ to $1.0\times10^{-7}$ m, preferably from $5\times10^{-8}$ to $1.5\times10^{-7}$ m, and
the value of external quantum efficiency is 0.6 or greater when a voltage of −2.6 V is applied between the second electrode (anode) and the first electrode (cathode) while irradiating light of 560 nm wavelength at 2 μW/cm².

[A05]
An image sensor including at least:
a first electrode;
a second electrode;
an organic photoelectric conversion layer; and
a carrier blocking layer,
in which the carrier blocking layer has a thickness of from $5\times10^{-9}$ to $1.0\times10^{-7}$ m, preferably from $5\times10^{-8}$ to $1.0\times10^{-7}$ m, and
the value of a dark current is $2.5\times10^{-10}$ A/cm² or smaller when voltages of from −1 to −10 V are applied between the second electrode (anode) and the first electrode (cathode).

[A06]
An image sensor including at least:
a first electrode;
a second electrode;
an organic photoelectric conversion layer; and
a carrier blocking layer,
in which the carrier blocking layer has a thickness of from $5\times10^{-9}$ to $1.0\times10^{-7}$ m, preferably from $5\times10^{-8}$ to $1.0\times10^{-7}$ m, and
when light of 560 nm wavelength is irradiated at 2 μW/cm² while applying −3 V between the second electrode and the first electrode and the irradiation of light is then stopped, $T_0$ is 10 milliseconds or less where $T_0$ is a time from the stop of the irradiation of light until a quantity of current decreases to $0.03\times I_0$ ($I_0$: quantity of current flowing between the second electrode and the first electrode immediately before the stop of the irradiation of light).

[A07]
An image sensor including at least:
a first electrode;
a second electrode;
an organic photoelectric conversion layer; and
a carrier blocking layer,
in which the carrier blocking layer has a thickness of from $5\times10^{-9}$ to $1.0\times10^{-7}$ m, preferably from $5\times10^{-8}$ to $1.0\times10^{-7}$ m, and
the carrier blocking layer has a light absorbance of 3% or less at 450 nm wavelength, 30% or less at 425 nm wavelength, and 80% or less at 400 nm wavelength.

[A08]
An image sensor including at least:
a first electrode;
a second electrode;
an organic photoelectric conversion layer; and
a carrier blocking layer,
in which the carrier blocking layer has a thickness of from $5\times10^{-9}$ to $1.0\times10^{-7}$ m, preferably from $5\times10^{-8}$ to $1.0\times10^{-7}$ m, and
the carrier blocking layer is formed of a material having a carrier mobility of $9\times10^{-4}$ cm²/V·s or higher, preferably $9\times10^{-3}$ cm²/V·s or higher, more preferably $6\times10^{-2}$ cm²/V·s or higher.

[A09]
The image sensor as described in any one of [A01] to [A08], in which the first electrode serves as a cathode, and the second electrode serves as an anode, and
the carrier blocking layer is arranged between the first electrode and the organic photoelectric conversion layer.

[A10]
The image sensor as described in any one of [A01] to [A09], in which the carrier blocking layer has a light absorbance of 3% or less at 450 nm wavelength, 30% or less at 425 nm wavelength, and 80% or less at 400 nm wavelength.

[A11]
The image sensor as described in any one of [A01] to [A10], in which the carrier blocking layer is formed of a material having a carrier mobility of $9 \times 10^{-4}$ cm$^2$/V·s or higher, preferably $9 \times 10^{-3}$ cm$^2$/V·s or higher, more preferably $6 \times 10^{-2}$ cm$^2$/V·s or higher.

[A12]
The image sensor as described in any one of [A01] to [A11], in which when light of 560 nm wavelength is irradiated at 2 μW/cm$^2$ while applying −3 V between the second electrode and the first electrode and the irradiation of light is then stopped, $T_0$ is 10 milliseconds or less where $T_0$ is a time from the stop of the irradiation of light until a quantity of current decreases to $0.03 \times I_0$ ($I_0$: quantity of current flowing between the second electrode and the first electrode immediately before the stop of the irradiation of light).

[A13]
The image sensor as described in any one of [A01] to [A12], in which the first electrode and the second electrode are formed of a transparent conductive material.

[A14]
The image sensor as described in any one of [A01] to [A12], in which one of the first electrode and the second electrode is formed of a transparent conductive material, and the other electrode is formed of a metal material.

[A15]
The image sensor as described in [A14], in which the first electrode is formed of a transparent conductive material, and the second electrode is formed of Al, Al—Si—Cu or Mg—Ag.

[A16]
The image sensor as described in [A14], in which the second electrode is formed of a transparent conductive material, and the first electrode is formed of Al—Nd or ASC.

[B01] Stacked Imaging Device
A stacked imaging device including at least:
two image sensors as described in any one of [A01] to [A16].

[C01] Imaging Module: First Aspect
An imaging module including:
a plurality of image sensors as described in any one of [A01] to [A16].

[C02] Imaging Module: Second Aspect
An imaging module including:
a plurality of stacked imaging devices as described in [B01].

REFERENCE SIGNS LIST

11 . . . Image sensor, 20 . . . Substrate, 21 . . . First electrode (cathode), 22 . . . Carrier blocking layer (first carrier blocking layer), 23 . . . Organic photoelectric conversion layer, 24 . . . Second carrier blocking layer, 25 . . . Second electrode (anode), 31 . . . Insulating layer, 40 . . . Imaging module, 41 . . . Imaging region, 42 . . . Vertical drive circuitry, 43 . . . Column signal processing circuitry, 44 . . . Horizontal drive circuitry, 45 . . . Output circuitry, 46 . . . Control circuitry, 47 . . . Vertical signal line, 48 . . . Horizontal signal line

What is claimed is:
1. An image sensor comprising at least:
a first electrode;
a second electrode;
an organic photoelectric conversion layer; and
a carrier blocking layer,
wherein the carrier blocking layer is formed of a material having the following structural formula (1), and has a thickness of from $5 \times 10^{-9}$ to $1.5 \times 10^{-7}$ m:

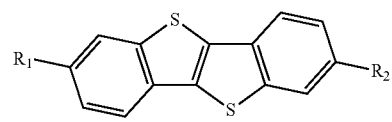

(1)

wherein $R_1$ and $R_2$ are independently a group selected from H, an aryl group and an alkyl group,
the aryl group is a group selected from the group consisting of phenyl, biphenyl, terphenyl, naphthyl, naphthylphenyl, tolyl, xylyl, $C_2$-$C_6$ alkyl-substituted phenyl, anthracenyl, anthracenylphenyl, phenanthryl, phenanthrylphenyl, pyrenyl, pyrenylphenyl, tetracenyl, tetracenylphenyl, fluoranthenyl, fluoranthenylphenyl, pyridinyl, pyridinylphenyl, quinolinyl, quinolylphenyl, acridinyl, acridinylphenyl, indol, indolylphenyl, imidazol, imidazolylphenyl, benzimidazole, benzimidazolylphenyl, thienyl, and thienyelphenyl,
the alkyl group is a group selected from the group consisting of methyl, ethyl, propyl, butyl, pentyl, and hexyl, which is a straight-chain alkyl group or a branched alkyl group, and
the second electrode is formed of a transparent conductive material, and the first electrode is formed of Al—Nd or ASC.

2. The image sensor according to claim 1, wherein the first electrode serves as a cathode, and the second electrode serves as an anode, and the carrier blocking layer is arranged between the first electrode and the organic photoelectric conversion layer.

3. The image sensor according to claim 1, wherein the carrier blocking layer has a light absorbance of 3% or less at 450 nm wavelength, 30% or less at 425 nm wavelength, and 80% or less at 400 nm wavelength.

4. The image sensor according to claim 1, wherein the carrier blocking layer is formed of a material having a carrier mobility of $9 \times 10^{-4}$ cm$^2$/V·s or higher.

5. The image sensor according to claim 1, wherein when light of 560 nm wavelength is irradiated at 2 μW/cm$^2$ while applying −3 V between the second electrode and the first electrode and the irradiation of light is then stopped, $T_0$ is 10 milliseconds or less where $T_0$ is a time from a stop of the irradiation of light until a quantity of current decreases to $0.03 \times I_0$ ($I_0$: quantity of current flowing between the second electrode and the first electrode immediately before the stop of the irradiation of light).

6. A stacked imaging device comprising at least:
two image sensors as defined in claim 1.

7. An imaging module comprising:
a plurality of image sensors as defined in claim 1.

8. An imaging module comprising:
a plurality of stacked imaging devices as defined in claim 6.

9. An image sensor comprising at least:
a first electrode;
a second electrode;
an organic photoelectric conversion layer; and
a carrier blocking layer, wherein the carrier blocking layer is formed of a material having the following structural formula (2), and has a thickness of from $5\times10^{-9}$ to $1.5\times10^{-7}$ m:

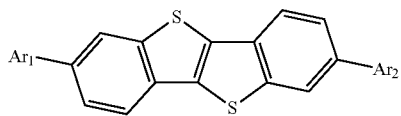

(2)

wherein $Ar_1$ and $Ar_2$ are independently a substituted or unsubstituted aryl group, which is selected from the group consisting of phenyl, biphenyl, terphenyl, naphthyl, naphthylphenyl, tolyl, xylyl, $C_2$-$C_6$ alkyl-substituted phenyl, anthracenyl, anthracenylphenyl, phenanthryl, phenanthrylphenyl, pyrenyl, pyrenylphenyl, tetracenyl, tetracenylphenyl, fluoranthenyl, fluoranthenylphenyl, pyridinyl, pyridinylphenyl, quinolinyl, quinolylphenyl, acridinyl, acridinylphenyl, indol, indolylphenyl, imidazol, imidazolylphenyl, benzimidazole, benzimidazolylphenyl, thienyl, and thienyelphenyl, and the second electrode is formed of a transparent conductive material, and the first electrode is formed of Al—Nd or ASC.

10. An image sensor comprising at least:
a first electrode;
a second electrode;
an organic photoelectric conversion layer; and
a carrier blocking layer,
wherein the carrier blocking layer is formed of a material having the following structural formula (3), and has a thickness of from $5\times10^{-9}$ to $1.5\times10^{-7}$ m:

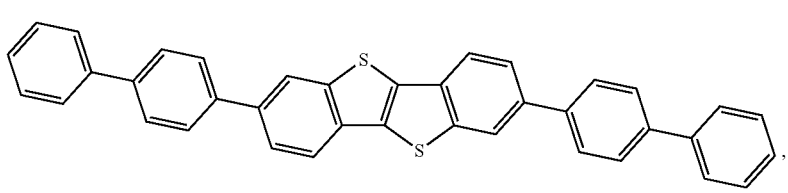

(3)

and
the second electrode is formed of a transparent conductive material, and the first electrode is formed of Al—Nd or ASC.

* * * * *